(12) United States Patent
Atzler et al.

(10) Patent No.: US 12,709,724 B2
(45) Date of Patent: Aug. 18, 2026

(54) MICROPLATES FOR AUTOMATING ORGANOID CULTIVATION

(71) Applicant: Molecular Devices (Austria) GmbH, Hallein (AT)

(72) Inventors: Josef Atzler, Hallein (AT); Felix Spira, Wallersee (AT); Andreas Kenda, Woerthersee (AT)

(73) Assignee: Molecular Devices (Austria) GmbH (AT)

( * ) Notice: Subject to any disclaimer, the term of this patent is extended or adjusted under 35 U.S.C. 154(b) by 799 days.

(21) Appl. No.: 17/508,193

(22) Filed: Oct. 22, 2021

(65) Prior Publication Data

US 2022/0127553 A1 Apr. 28, 2022

Related U.S. Application Data

(60) Provisional application No. 63/094,946, filed on Oct. 22, 2020.

(51) Int. Cl.
*C12M 3/00* (2006.01)
*C12M 1/00* (2006.01)
(Continued)

(52) U.S. Cl.
CPC ............ *C12M 21/08* (2013.01); *C12M 23/12* (2013.01); *C12M 23/22* (2013.01); *C12M 23/24* (2013.01);
(Continued)

(58) Field of Classification Search
CPC ...... C12M 21/08; C12M 23/12; C12M 23/22; C12M 23/24; C12M 23/34; C12M 25/00; C12M 29/10; C12M 33/08
See application file for complete search history.

(56) References Cited

U.S. PATENT DOCUMENTS

D414,271 S 9/1999 Mendoza
5,962,250 A * 10/1999 Gavin .................. B01L 3/5025 435/395

(Continued)

FOREIGN PATENT DOCUMENTS

CN 104936698 A 9/2015
CN 105209595 A 12/2015

(Continued)

OTHER PUBLICATIONS

Clinton, James et al., “Initiation Expansion, and Cryopreservation of Human Primary Tissue-Derived Normal and Diseased Organoids in Embedded Three-Dimensional Culture”, Current Protocols in Cell Biology, vol. 82, No. 1, Mar. 30, 2019, 22 pages.

(Continued)

*Primary Examiner* — Michael A Marcheschi
*Assistant Examiner* — Ashley Lopezlira
(74) *Attorney, Agent, or Firm* — Merchant & Gould P.C.

(57) ABSTRACT

Disclosed are various embodiments for growing, culturing, monitoring, and analyzing embryoid bodies, fused embryoid bodies, spheroids, organoids, or other multi-cellular bodies using a system of microplates. Different types of microplates are designed to be used during the various stages of growing and culturing of cells to form embryoid bodies, fused embryoid bodies, spheroids, organoids, or other multi-cellular bodies. The different microplates are designed to mate with one another to allow for the transfer of cells from wells in one plate to wells in the other plate. An assay plate includes an array of perfusable units that include a supply well that is in fluid communication with a culture well to allow for an exchange of fluid.

11 Claims, 22 Drawing Sheets

(51) Int. Cl.
*C12M 1/04* (2006.01)
*C12M 1/12* (2006.01)
*C12M 1/26* (2006.01)
*C12M 1/32* (2006.01)

(52) U.S. Cl.
CPC ............ *C12M 23/34* (2013.01); *C12M 25/00* (2013.01); *C12M 29/10* (2013.01); *C12M 33/08* (2013.01)

(56) References Cited

U.S. PATENT DOCUMENTS

D420,743 S 2/2000 Monks
6,051,191 A 4/2000 Ireland
6,449,827 B1 9/2002 Clarke
D601,714 S 10/2009 Lohn
D628,305 S 11/2010 Gorrec
8,590,736 B2 11/2013 Motadel
D699,371 S 2/2014 Williams
D745,698 S 12/2015 Hage
D768,873 S 10/2016 Stedman
D840,053 S 2/2019 Kamees
D911,285 S 2/2021 Manuel
D920,536 S 5/2021 Self
D954,985 S 6/2022 Grayson
D956,263 S 6/2022 Beckett
D968,644 S 11/2022 Schatilov
D1,098,489 S 10/2025 Paccaud
D1,099,360 S 10/2025 Matsumoto
D1,101,188 S 11/2025 Hendrikx
D1,116,154 S 3/2026 Hendrikx
2003/0170883 A1 9/2003 Martin
2005/0023448 A1 2/2005 Ogawara et al.
2005/0287573 A1* 12/2005 Stafslien ................ C12M 33/00 435/6.19
2006/0234370 A1* 10/2006 Korpinen ............... C12M 23/46 435/287.2
2007/0154356 A1 7/2007 Modavis
2009/0286317 A1* 11/2009 Demmler ............... C12M 25/14 435/303.1
2010/0258578 A1* 10/2010 Motadel ................. G01N 35/04 221/92
2014/0322806 A1* 10/2014 Bennett ................ C12N 5/0602 435/325
2016/0075985 A1* 3/2016 Jung ...................... C12M 21/18 435/32
2017/0276682 A1* 9/2017 Park ................. G01N 33/57492
2018/0142196 A1* 5/2018 Coppeta ................. C12M 23/12
2019/0002809 A1* 1/2019 Oakley .............. G01N 33/5014
2019/0249126 A1* 8/2019 Mackowiak ............. C12M 1/12
2019/0390149 A1* 12/2019 Cho ....................... C12M 23/12
2020/0063081 A1 2/2020 Vulto
2020/0208089 A1 7/2020 Hung
2020/0354668 A1* 11/2020 Sawyer .................. C12M 25/14
2020/0408695 A1 12/2020 Dragna
2021/0002688 A1* 1/2021 Corwin .................. C12M 23/16
2021/0069697 A1* 3/2021 Azizgolshani ......... C12M 41/08
2021/0292707 A1 9/2021 Von Guttenberg et al.
2021/0395658 A1 12/2021 Takahashi
2022/0017846 A1 1/2022 Vulto
2023/0226542 A1 7/2023 Atzler
2025/0161950 A1 5/2025 Horak
2025/0235872 A1 7/2025 Jeffrey-Coker

FOREIGN PATENT DOCUMENTS

CN 108699500 A 10/2018
CN 111996121 A 11/2020
CN 202130412710.6 1/2022
DE 4120303 12/1992
DE 69109651 9/1995
DE 202017003978 8/2017
EP 0094216 A1 11/1983
EP 359249 3/1990
EP 3124591 2/2017
GB 2028869 A 3/1980
JP 2012-060903 A 3/2012
JP D2011-24238 9/2012
KR 20170142729 12/2017
KR 102127765 6/2020
KR 102127765 B1 6/2020
RU 2668157 C1 9/2018
WO 20150009893 1/2015
WO 2016195480 A1 12/2016
WO 2017091075 A1 1/2017
WO 2017/198987 11/2017
WO 2017/216113 A2 12/2017
WO 2019/178039 9/2019
WO 2020/013851 1/2020
WO 2020/160678 8/2020
WO 2020/0225777 11/2020

OTHER PUBLICATIONS

PCT International Search Report and Written Opinion in International Application PCT/IB2021/059782, mailed Feb. 22, 2022, 14 pages.
Dumont et al., “Human cell lines for biopharmaceutical manufacturing: history, status, and future perspectives”, Critical Reviews in Biotechnology, Nov. 1, 2016; 36(6): 1110-1122.
LeSavage et al., “Next-generation cancer organoids”, Nature Materials 21, 143-159 (2022).
Llames, Sara et al., “Feeder Layer Cell Actions and Applications”, Tissue Engineering: Part B, vol. 21, No. 4, 2015, 345-353.
Microplates. Online, published date unknown, Retrieved on Apr. 19, 2023 from URL: https://www.fishersci.com/us/en/browse/90111007/microplates?page=1.
PCT International Preliminary Report on Patentability in International Application PCT/IB2021/059782, mailed May 4, 2023, 7 pages.
Thermo Scientific Nunc Microwell 96-Well, Nunclon Delta-Treated, Flat-Bottom Microplate, Online, published date unknown. Retrieved on Apr. 19, 2023 from URL: https://fishersci.com/shop/products/nunc-microwell-96-well-nunclon-delta-treated-flat-bottom-microplate-1/1256626?gclid=CjwKCAjwov6hBhBsEiwArvN6LbMOGGT.
ThermoFisher Scientific, “3D cell culture handbook”, 2020, 124 pages.
Yuki, Kanako et al., “Organoid Models of Tumor Immunology”, Trends Immunol, Aug. 2020; 41(8):652-664.
He Yi; Liang Jie, “Preliminary Construction and Evaluation of a PDMS Microwell Array Cell Culture Experimental Platform”, Journal of Tissue Engineering and Reconstructive Surgery, Jun. 15, 2011, Issue 3, pp. 121-128.
“Plates”, Online, publish date unknown. Retrieved on Mar. 3, 2026 from URL: https://www.sigmaaldrich.com/US/en/ products/labware/plates?srsltid=AfmBOopx7dDnA6fZqx7FNR8mPXh5LTuhq6RzFE1x5L_U2vHpD-3y0Wxl, 2 pages.
Extraction of three dimensional stuctures from corning matrigel matrix, 2019, URL: https://www.corning.com/catalog/cls/documents/protocols/CLS-AN-528.pdf, 1 page.
Chinese First Office Action in Application 202180083552.1, mailed Apr. 23, 2026, 21 pages.

* cited by examiner

MICROPLATES FOR AUTOMATING ORGANOID CULTIVATION

CROSS-REFERENCE TO RELATED APPLICATIONS

This application claims priority to, and the benefit of, U.S. Provisional Patent Application No. 63/094,946 filed Oct. 22, 2020, the disclosure of which is hereby incorporated by reference herein in its entirety.

INTRODUCTION

Culturing cells in a three-dimensional (3D) environment yields cellular behavior and morphology that more closely matches what is observed in the human body. 3D hydrogels/hyrdoscaffolds used for this kind of culturing have a unique attribute: cells can be deposited in specific locations in 3D space and remain in position for extended time periods. This enables the creation of structures (e.g., embryoid bodies, fused embryoid bodies, spheroids, organoids, and/or other multi-cellular bodies) and co-culture environments where cellular interactions and developments over time are observed. While strides have been made in the use of 3D hydrogels/hyrdoscaffolds for 3D culture of cellular bodies, growing cellular bodies of suitable size and type that remain healthy and retain longevity for biochemical assays remains challenging. Such culture also is very time and labor intensive.

SUMMARY

In one aspect, the technology relates to a tissue culture kit for growing organoids, including: a combination plate including an array of wells; and an assay plate including an array of perfusable units, each perfusable unit includes a respective culture well and a respective supply well that are fluidly connected to one another, a positioning of the array of perfusable units mirroring the positioning of the array of wells of the combination plate, thereby allowing respective ones the array of perfusable units to mate with the array of wells of the combination plate. In an example, the array of wells includes a first array of wells, and further includes: a starter plate including a second array of wells, a positioning of the second array of wells of the starter plate mirroring a positioning of the first array of wells of the combination plate, thereby allowing respective ones of the first array of wells to mate with corresponding ones of the second array of wells. In another example, individual wells of the second array of wells of the starter plate include a respective starter plate mating collar being sized and shaped to create an interference fit with a respective combination plate mating collar of individual wells of the first array of wells. In yet another example, a size of the respective starter plate mating collar is smaller than a size of the respective combination plate mating collar. In still another example, the starter plate mates with the combination plate to allow for a transfer of one or more cells from a respective well in the first array of wells to a respective corresponding well in the second array of wells.

In another aspect of the above aspect, individual wells of the array of wells includes a respective combination plate mating collar that is sized and shaped to create an interference fit with a respective third opening of a respective well of a respective perfusable unit of the array of perfusable units. In an example, the combination plate mates with the assay plate to allow for a transfer of one or more cells from a respective corresponding well of the array of wells into a respective culture well of the assay plate. In another example, the combination plate and the assay plate each include a respective alignment pin and a respective alignment receiving aperture. In yet another example, the combination plate is inverted relative to the assay plate when interconnected with the assay plate. In still another example, the assay plate further includes an optically transparent viewing surface forming a bottom surface of the array of perfusable units.

In another example of the above aspect, the optically transparent viewing surface is gas permeable.

In another aspect, the technology relates to a method for transferring one or more cells between tissue culture plates, the method includes: aligning an inverted first plate having a first array of wells over a non-inverted second plate having a second array of wells, the one or more cells being included in at least one well of the first array of wells; mating the inverted first plate with the non-inverted second plate by interconnecting the first array of wells of the inverted first plate with the second array of wells of the non-inverted second plate; and agitating the mated plates to transfer the one or more cells included in the at least one well of the first array of wells into a corresponding at least one well of the second array of wells. In an example, the method further includes culturing the one or more cells in the first plate over a first incubation period in a growth medium; and inverting the first plate following the first incubation period. In another example, agitating the mated plates includes applying ultrasonic impulses to the first plate to cause the one or more cells in the at least one well to fall into the corresponding at least one well of the second plate. In yet another example, the method further includes adding a hydrogel to the at least one well of the second array of wells prior to mating the first array of wells with the second array of wells. In still another example, the at least one well of the second plate includes at least one other cell, the one or more cells in the at least one well of the first plate being transferred into the at least one well of the second plate to form at least one organoid with the at least one other cell.

In another example of the above aspect, the method further includes culturing the one or more cells in the second well of the second plate over a second incubation time; inverting the second plate; mating the second plate with a non-inverted third plate; and agitating the mated second plate and the non-inverted third plate to transfer the one or more cells from the at least one well of the second plate into at least one culture well of the non-inverted third plate.

In another aspect, the technology relates to an arrangement of cell-culturing plates to allow for a transfer of one or more cells, including: a first plate including a first array of wells, at least one well in the first array of wells includes at least one embryoid body; and a second plate mated with the first plate, the second plate includes a second array of wells that are interconnected with the first plate to form an interference fit. In an example, the first plate is mated with the second plate for transfer of the at least one embryoid body from the at least one well in the first array of wells into at least one corresponding well of the second array of wells. In another example, the at least one corresponding well of the second array of wells contains at least one other embryoid body prior to the transfer of the at least one embryoid body from the at least one first well of the first array of wells.

In another aspect, the technology relates to an assay plate for culturing organoids, the assay plate includes: a well plate including an array of perfusable units, individual perfusable units include a culture well fluidly connected to a supply well via at least one channel, the at least one channel being sized and shaped to allow a gravitational flow of liquid between the culture well and the supply well through the at least one channel; and a bottom layer sheet disposed on an underside of the well plate forming a bottom layer for the array of perfusable units. In an example, the bottom layer sheet includes an optically transparent viewing window. In another example, the bottom layer sheet is gas permeable, thereby allowing oxygen to flow to cellular aggregates growing in one or more of the perfusable units. In yet another example, a volume of the culture well is larger than a volume of the supply well. In still another example, the culture well and the supply well share a portion of at least one sidewall defining the culture well and the supply well, a remaining portion of the at least one sidewall of the culture well and the supply well extending a length that is greater than a length of the shared portion of at least one sidewall.

In another example of the above aspect, the at least one channel is formed by a gap between an end of the portion of the at least one sidewall and the bottom layer sheet. In an example, a respective culture well or a respective supply well of at least one perfusable unit of the array of perfusable units further includes a barrier wall extending orthogonally away from the bottom layer sheet, wherein the at least one channel is further defined by a volume between the barrier wall and the shared portion of the at least one sidewall. In another example, the at least one channel includes a plurality of microchannels that are sized and shaped to prevent migration of one or more embryoids from the culture well into the supply well. In yet another example, the assay plate further includes a hydrogel within the culture well.

In another aspect, the technology relates to a method, including: introducing a hydrogel into a culture well of a perfusable unit of an assay plate, the culture well being in fluid communication with a supply well via at least one channel; introducing at least one embryoid into the hydrogel through the culture well; introducing feeding media into the supply well of the perfusable unit; and tilting the assay plate, thereby causing a gravitational flow of the feeding media between the culture well and the supply well via the at least one channel. In an example, the assay plate is tilted on a tilting platform. In another example, the at least one embryoid is sized greater than 100 micrometers in diameter. In yet another example, the assay plate includes a plurality of perfusable units, and a subset of the plurality of perfusable units being fluidly connected to one another, and the feeding media flowing through each of perfusable units of the subset of perfusable units in response to tilting of the assay plate. In still another example, individual perfusable units in the subset of perfusable units include one or more different types of embryoids.

In another example of the above aspect, the hydrogel is introduced into the culture well in liquid form and, when introduced into the culture well, a portion of the hydrogel flows into the supply well via the at least one channel. In an example, the supply well includes a barrier wall disposed between a primary volume of the supply well and the channel, and the portion of the hydrogel flows into the supply well up to the barrier wall. In another example, the method further includes imaging the organoid in situ in the culture well.

In another aspect, the technology relates to a system, including: a tilting platform; and an assay plate situated on the tilting platform, the assay plate includes a plurality of perfusable units, each of the perfusable units having a respective culture well and a respective supply well, the respective culture well and the respective supply well being fluidly connected with one another via at least one channel that facilitates a gravitational flow of liquid between the respective culture well and the respective culture well in response to a tilting of the assay plate via the tilting platform. In an example, the system further includes hydrogel disposed within a bottom surface of the respective culture well. In another example, the assay plate further includes a transparent gas permeable surface disposed on an underside of the assay plate and forming a bottom portion of the plurality of perfusable units.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1:
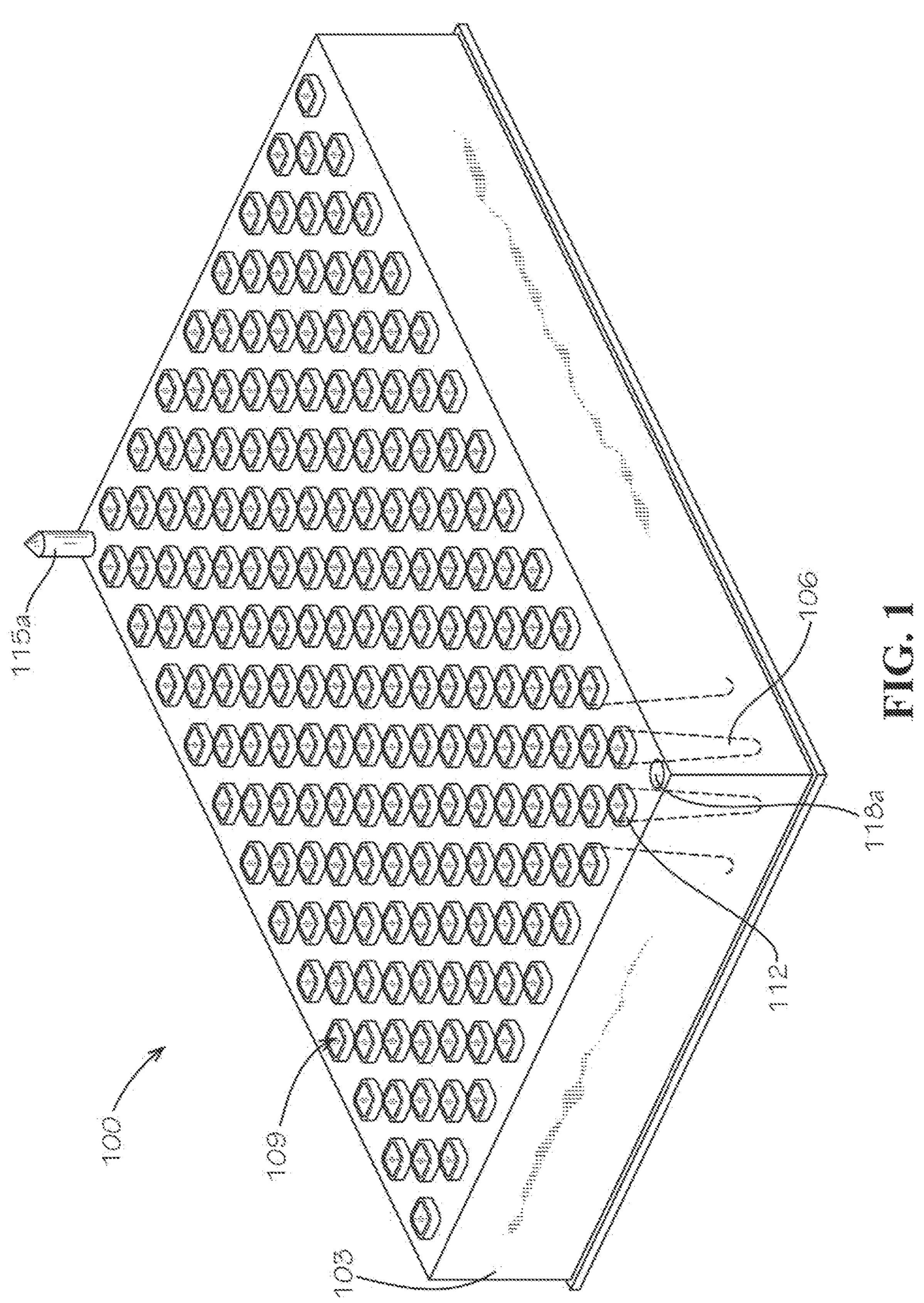
FIG. 1 illustrates an example of a perspective view of a starter microplate according to various embodiments of the present disclosure.

The present disclosure relates to growing, culturing, monitoring, and analyzing of embryoid bodies, fused embryoid bodies, spheroids, organoids, and/or other multicellular bodies in vitro using a system of microplates according to various embodiments. In particular, different types of microplates are designed to be used during the various stages of growing and culturing of cells to form embryoid bodies, fused embryoid bodies, spheroids, organoids, and/or other multi-cellular bodies. According to various embodiments, the microplates of the present disclosure are designed to facilitate the creation of cellular bodies though: cell culture with one or more cells, cell culture with one or more types of cells, the combination of cell cultures, the embedding of fused cell cultures into a hydrogel, and the transfer of cell cultures between the various microplates of the present disclosure. In addition, in various embodiments, the system of microplates can be used to grow embryoid bodies, fused embryoid bodies, spheroids, organoids, and/or other multi-cellular bodies of about 25 to 4000 micrometers (μm) in diameter.

Described herein are multi-well microplates that facilitate 3D tissue culture, in particular the growth and maintenance of cellular bodies (e.g., embryoid bodies, fused embryoid bodies, spheroids, organoids, or other multi-cellular bodies). Multi-well microplates as described herein can be a starter plate to facilitate the growth of a 3D body of cells from one or more single cells (or a plurality of single, dissociated, cells); a combination plate that enables the fusing of two or more cellular bodies; and an assay plate that comprises one or more perfusable units, thereby providing wells that are sized appropriately to enable the growth of cellular bodies in addition to providing perfusion of fresh media to supply nutrients to and remove waste from the cellular bodies. According to embodiments of the present disclosure, each of the plates can be physically compatible with the other plates (or other types of plates) so that they may be physically interconnected (e.g., mated together, for example with one plate inverted relative to the other with each respective well of one plate fluidly connected with the corresponding respective well of another plate).

In embodiments, the perfusable unit of the assay plate can comprise a growth well (or culture well) and a supply well (or feeder well) that are interconnected by a gap and/or channel. In embodiments, the assay plate can comprise an array of two or more perfusable units that are interconnected by two or more channels.

According to various embodiments, described herein are tissue culture kits. According to various embodiments, a tissue culture kit can comprise a starter kit, a combination kit, and an assay kit. According to various embodiments, an assay microplate included in a kit of tissue culture microplates of the present disclosure is designed for growing and monitoring embryoid bodies, fused embryoid bodies, spheroids, organoids, and/or other multi-cellular bodies. In addition, the assay microplate of the present disclosure is designed to allow observation of organoids in hydrogel that may be in contact with two different liquids to create a gradient of concentrations within the hydrogel. In particular, the assay microplate of the present disclosure comprises perfusable units having double wells (e.g., a supply well and a culture well) that are fluidly connected to one another to allow a perfusive flow of liquid from one well to the other in response to tilting of the plate (gravity flow). In various embodiments, the assay microplate further provides a transparent sealing layer that forms the bottom layer for the array of perfusable units. In various embodiments, the transparent sealing layer may be gas permeable to support transport of oxygen to the surface of the organoid. In various embodiments, the sealing layer comprises a transparent viewing window. The viewing window can be a window that is suitable for microscopic observation, whether brightfield, phase-contrast, fluorescent, confocal, two-photon, or other microscopic imaging modalities as known in the art. In some embodiments, each growth well of a perfusable unit can comprise a transparent viewing window. In various embodiments, at least one growth well of a perfusable unit of an array of perfusable units can comprise a transparent viewing window.

As used herein, “stem cell” refers to an undifferentiated or partially differentiated (pluripotent or multipotent, respectively) cell that can proliferate indefinitely and differentiate into a primary adult cell, adult cell, or any kind of differentiated tissue of the same or different cellular lineage. Stem cells as described herein can be embryonic or formed by reprogramming to become an induced pluripotent stem cell, although other sources of stem cells known in the art are present (such as from cord blood).

As used herein, “embryoid” or “embryoid body” refers to a three-dimensional aggregate of cells (e.g., pluripotent or multipotent stem cells). Embryoid bodies according to the present disclosure are structures in suspension that can respond to extracellular cues and differentiate into a structure of any of the three germ layers (endodermal, ectodermal, or mesodermal) and can be embedded in hydrogels or scaffolds for further differentiation into organoids.

As used herein, “organoid” refers to a miniaturized and simplified version of an organ produced in vitro in three dimensions that shows realistic micro-anatomy or reflects one or more functions of an organ. As described herein, organoids can be derived from one or a few cells from a tissue, embryonic stem cells or induced pluripotent stem cells, which can self-organize in three-dimensional culture owing to their self-renewal and differentiation capacities. An organoid may refer to a cellular aggregate that fulfills one or more functions of an organ.

Starter Plate

Turning now to FIG. 1, shown is an example of a starter microplate 100 that may be included in the kit of tissue culture microplates, in accordance with various embodiments of the present disclosure. According to various examples, the starter microplate 100 can be used as a starter plate for growing cells that can be used to form embryoid bodies, fused embryoid bodies, spheroids, organoids, and/or other multi-cellular bodies. FIG. 1 illustrates an example of a perspective view of a starter microplate 100, FIG. 2A illustrates an example of a cross sectional view of a single row of the starter microplate 100, and FIG. 2B illustrates an example of a top view of the starter microplate 100, in accordance with various embodiments of the present disclosure.

The starter microplate 100 comprises a well plate 103 having a plurality of starter plate wells 106 for culturing cells in a three-dimensional (3D) cell growth medium. In various examples, the well plate 103 comprises a top surface and a thickness corresponding to a desired well height. The components of well plate 103 may be formed of any suitable material by any suitable procedures. In exemplary embodiments, the well plate 103 may be formed of polymer, such as a transparent polymer, and/or other material as can be appreciated. For example, the polymer may comprise polystyrene, polypropylene, poly(methyl methacrylate), cyclic olefin polymer, cyclic olefin copolymer, and/or other polymer as can be appreciated. The well plate 103 may have no removable/moving parts and/or may be formed as a single piece, such as by injection molding or 3D printing, such that all of the structures (e.g., wells) of the well plate 103 are formed integrally with one another.

Figure 2A:
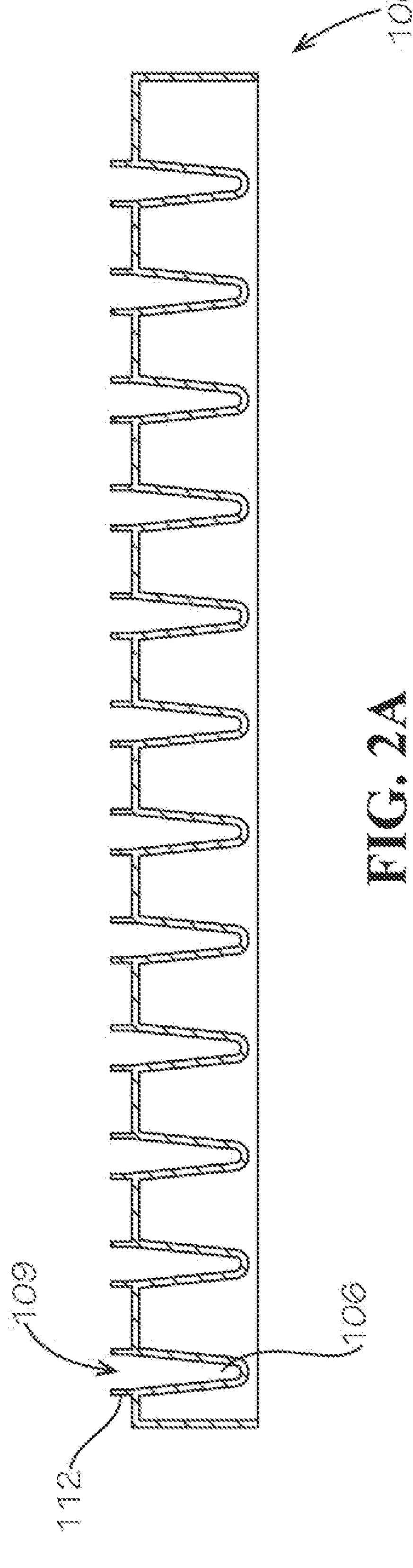
FIG. 2A illustrates an example of a cross sectional view of the starter microplate of FIG. 1 according to various embodiments of the present disclosure.
Figure 2B:
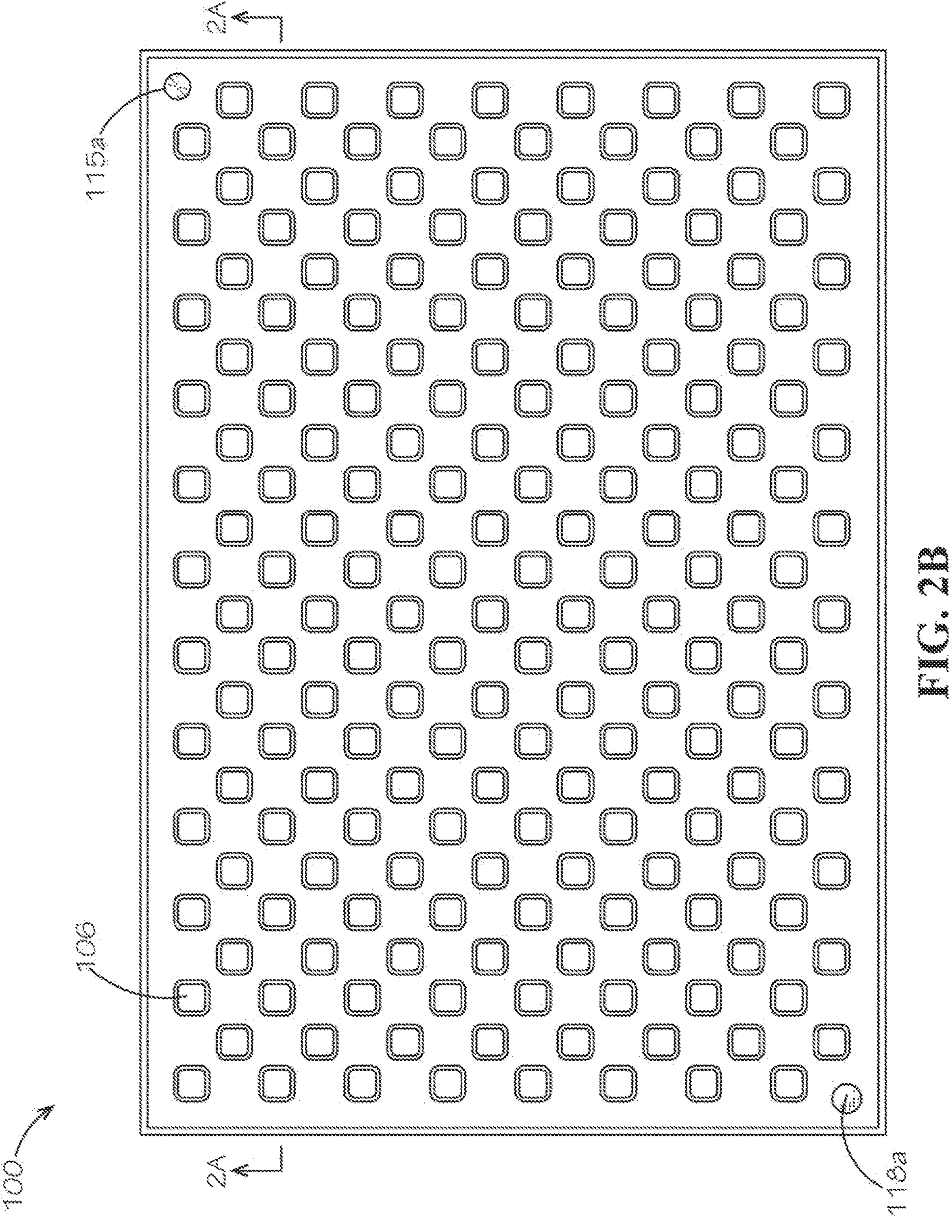
FIG. 2B illustrates an example of a top view of the starter microplate of FIG. 1 according to various embodiments of the present disclosure.

The starter plate wells 106 are preferably arrayed in columns and rows as depicted in FIGS. 1 and 2A. Each of the starter plate wells 106 include an orifice 109 formed by walls that extend from the top surface of the well plate 103 and extend toward a bottom surface of the starter plate wells 106. In one embodiment, the bottom surface of each of the starter plate wells 106 may extend to the bottom of the well plate 103. Alternatively, the starter plate wells 106 may not be as deep as the well plate 103. In one embodiment, the starter plate wells 106 may be suspended from the top surface of the well plate 103 where there is no bottom surface. The starter plate wells 106 may comprises a shape suitable for culturing cells. For example, the starter plate wells 106 may comprises a u-shaped well, a v-shaped well, or other shaped-well as can be appreciated. In various examples, the wells 106 are tapered so that the diameter or size of the top of the well differs from the diameter or size of the bottom of the well.

As can be appreciated, any suitable cells may be introduced to populate the wells 106 of the starter microplate 100. These cells may include stem cells (e.g., pluripotent stem cells), support cells, and/or the like. The cells may be deposited in a scaffold by any suitable technique including bioink droplet printing, micro-contact printing, photolithography, dip pen nanolithography, and/or pipetting, among others.

Furthermore, one or more growth factors may be introduced into the wells 106 of the starter microplate 100 in the form of a liquid medium. Exemplary growth factors that may be suitable include angiopoietin, bone morphogenetic proteins (BMPs), ciliary neurotropic factor, colony stimulating factors, ephrins, epidermal growth factor, erythropoietin, fibroblast growth factors, glial-derived neurotrophic factor, hepatocyte growth factor, insulin, insulin-like growth factors, interleukins, leukemia inhibitory factor, keratinocyte growth factor, neuregulins, neurotrophins, platelet-derived growth factor, transforming growth factors, tumor necrosis factor (alpha), vascular endothelial growth factor, and/or the like.

According to various embodiments, the starter microplate 100 is compatible with a combination microplate 300 (FIG. 3) of the system of microplates to facilitate the transfer of one or more cells from the starter microplate 100 to the combination microplate 300. For example, the starter microplate 100 may be mated with the combination microplate 300 to allow for the starter plate wells 106 of the starter microplate 100 to engage with or otherwise interconnect with corresponding combination plate wells 303 of the combination microplate 300. For example, a positioning of the combination plate wells 303 on the well plate 309 may mirror a positioning of the starter plate wells 106 on the starter well plate 103 to allow for an aligned mating of the combination plate wells 106 with the starter plate wells 106 as can be appreciated. As will be discussed in further detail below, this process can be achieved manually or automatically though the use of a robotic apparatus.

In various embodiments, the starter plate wells 106 each comprise a respective mating collar 112 that extends away from a top surface of the well plate 103, thereby extending the walls of the starter plate wells 106 of the corresponding starter plate well 106 from the top surface of the well plate 103. The mating collars 112 of the starter plate wells 106 of the starter microplate 100 are sized and shaped to fit within, or otherwise mate with, the well orifices 306 of the combination microplate 300. Accordingly, in various examples, a size (e.g., perimeter or circumference) of the mating collars 112 is smaller than a size (e.g., perimeter, circumference) of the well orifices 405 at the top surface of the well plate 103. In various embodiments, the mating collars 112 are sized and shaped to create an interference fit with the corresponding combination plate wells 303 of the combination microplate 300 to facilitate a leak-free transfer of the one or more cells and any associated liquid that is included in the respective starter plate well 106. In some examples, the mating collars 112 may further comprise a gasket (e.g., an o-ring), an array of gaskets, or other type of sealing structure that can sit between the mated plates to prevent spillage of fluid between the mated wells.

Figure 3:
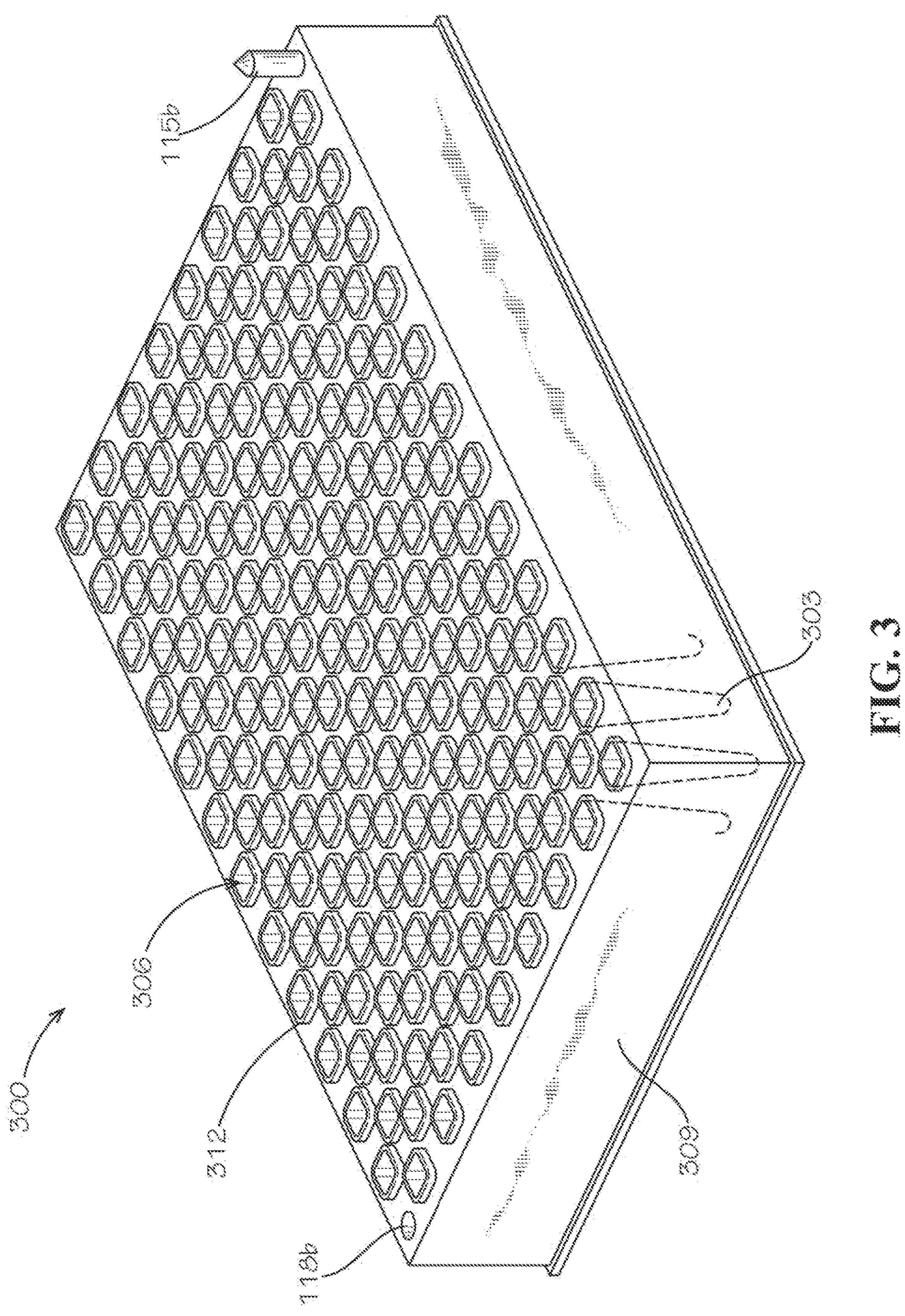
FIG. 3 illustrates an example of a perspective view of a combination microplate according to various embodiments of the present disclosure.

According to various embodiments, the starter microplate 100 further comprises an alignment guide 115*a* and an alignment receiving aperture 118*a* that are designed to facilitate an aligned placement of the starter microplate 100 over the combination microplate 300 when mating the starter microplate 100 with the combination microplate 300. In particular, the alignment guide 115*a* of the starter microplate 100 may comprise, for example, a pin that is sized and shaped to align with and engage with an alignment receiving aperture 118*b* (FIG. 3) that is included on the combination microplate 300. As depicted in FIG. 3, the combination microplate 300 further comprises an alignment guide 115*b* and an alignment receiving aperture 118*b*. It should be noted that although the placement of the alignment guides 115 and alignment apertures 118 of the starter microplate 100 and the combination microplate 300 are illustrated in FIGS. 1 and 3 as being opposing corners of the microplates 100, 300 to allow proper engagement when the starter microplate 100 is inverted and placed over the combination microplate 300, the positioning of the alignment guides 115 and receiving apertures 118 are not limited to the positions illustrated in the FIGS. 1 and 3 and may be positioned at any location on the plates that does not interfere with the wells.

Combination Plate

Figure 4A:
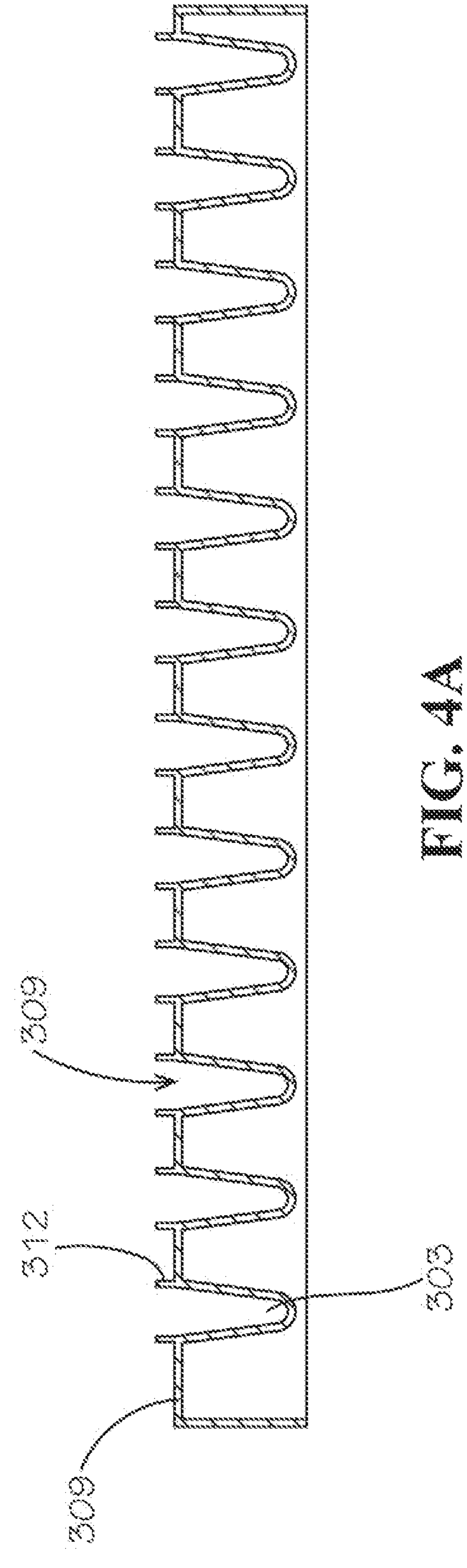
FIG. 4A illustrates a top view of the combination microplate of FIG. 3 according to various embodiments of the present disclosure.
Figure 4B:
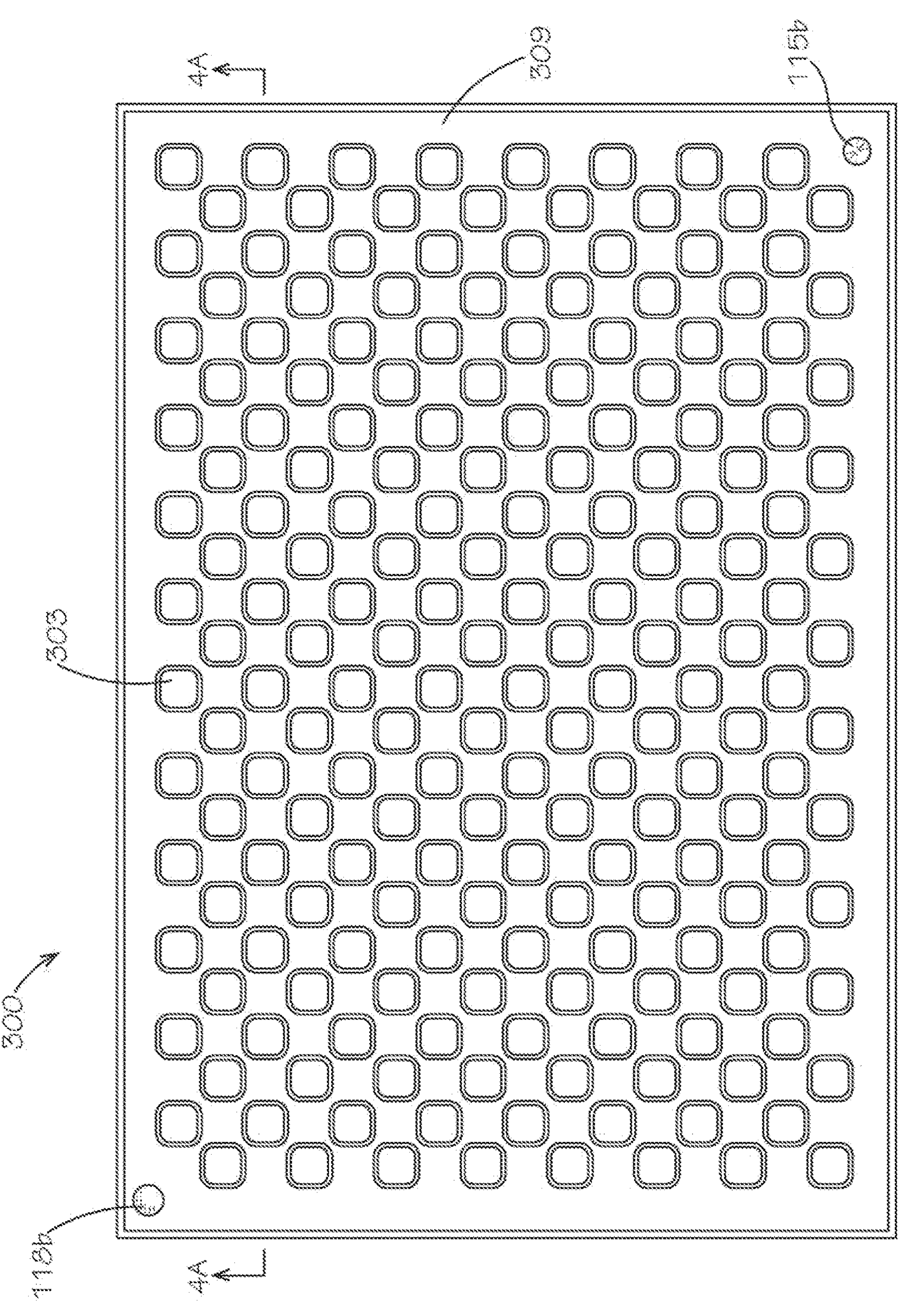
FIG. 4B illustrates an example of a cross-sectional view of the combination microplate of FIG. 3 according to various embodiments of the present disclosure.

Turning now to FIG. 3, shown is an example of a perspective view of a combination microplate 300 (e.g., a combination plate) that may be included in the kit of tissue culturing microplates, in accordance with various embodiments of the present disclosure. FIG. 4A illustrates a top view of the combination microplate 300 according to various embodiments, and FIG. 4B illustrates an example of a cross sectional view of the combination microplate 300 according to various embodiments of the present disclosure.

According to various examples, the combination microplate 300 can be used as a plate for growing cells that can be used to form organoids similarly to that of the starter microplate 100. In other various examples, the combination microplate 300 can further be used to combine or otherwise fuse cells (e.g., embryoid bodies) transferred from one or more starter microplates 100. For example, embryoid bodies can be transferred into a given well 303 of the combination microplate 300 via one or more starter microplates 100, thereby allowing the transferred embryoid bodies to fuse to one other with the intent of growing and creating spheroids/organoids, as can be appreciated.

The combination microplate 300 comprises a well plate 309 having a plurality of combination plate wells 303 for culturing cells in a 3D cell growth medium. In various examples, the well plate 309 comprises a top surface and a thickness corresponding to a desired well height. The components of well plate 309 may be formed of any suitable material by any suitable procedures. In exemplary embodiments, the well plate 309 may be formed of polymer, such as a transparent polymer. For example, the polymer may comprise polystyrene, polypropylene, poly(methyl methacrylate), cyclic olefin polymer, cyclic olefin copolymer, and/or other polymer as can be appreciated. The well plate 309 may have no removable/moving parts and/or may be formed as a single piece, such as by injection molding, 3D printing, or other approach such that all of the structures (e.g., compartments) of the well plate 309 are formed integrally with one another.

The combination plate wells 303 are preferably arrayed in columns and rows as depicted in FIGS. 3 and 4A. According to various examples, a positioning of the combination plate wells 303 on the well plate 309 mirror a positioning of the starter plate wells 106 on the starter well plate 103 to allow for an aligned mating of the combination plate wells 106 with the starter plate wells 106 as can be appreciated. Each of the combination plate wells 303 include an orifice 306 formed by walls that extend from a top surface to a bottom surface of the combination plate wells 303. In one embodiment, the bottom surface of each of the starter plate wells 303 may extend to the bottom of the well plate 309. Alternatively, the combination plate wells 303 may not be as deep as the well plate 309. The combination plate wells 303 may comprises a shape suitable for culturing cells. For example, the combination plate wells 303 may comprises a u-shaped well, a v-shaped well, or other shaped-well as can be appreciated. In various examples, the wells 303 are tapered so that the diameter or size of the top of the well differs from the diameter or size of the bottom of the well.

As can be appreciated, any suitable cells may be introduced to populate the wells 303 of the combination microplate 300. These cells may include stem cells (e.g., pluripotent stem cells), support cells, and/or the like. In some embodiments, the cells may be deposited in a scaffold by any suitable technique including bioink droplet printing, micro-contact printing, photolithography, dip pen nanolithography, and/or pipetting, among others. In other embodiments, the cells may be deposited into the wells of the combination microplate 300 in response to mating one or more starter microplates 100 with the combination microplate 300 and causing the cells in the starter microplate 100 to transfer to the combination microplate 300 in accordance with various embodiments of the present disclosure. For example, as will be discussed, ultrasonic impulses can be applied to the mated plates to reduce the surface tension associated with the cells in the starter microplate 100, thereby allowing the cells and any corresponding medium to transfer from the starter microplate 100 to the combination microplate 300.

Furthermore, one or more growth factors may be introduced into the wells 303 of the combination microplate 300 in the form of a liquid medium. Exemplary growth factors that may be suitable include angiopoietin, bone morphogenetic proteins (BMPs), ciliary neurotropic factor, colony stimulating factors, ephrins, epidermal growth factor, erythropoietin, fibroblast growth factors, glial-derived neurotrophic factor, hepatocyte growth factor, insulin, insulin-like growth factors, interleukins, leukemia inhibitory factor, keratinocyte growth factor, neuregulins, neurotrophins, platelet-derived growth factor, transforming growth factors, tumor necrosis factor (alpha), vascular endothelial growth factor, and/or the like.

According to various embodiments, the combination microplate 300 is compatible with an assay microplate 500 (FIG. 5) of the kit of tissue culture microplates to facilitate the transfer of one or more cells from the combination microplate 300 to the assay microplate 500. In various examples, the combination microplate 300 can mate with the assay microplate 500 to facilitate the transfer of embryoid bodies from the combination microplate 300 into the assay microplate 500. For example, the combination microplate 300 can be inverted and placed over the assay microplate 500 to allow for the combination plate wells 303 to engage with, mate with, or otherwise interconnect with a perfusable unit 503 (FIG. 5) of the assay microplate 500.

In various embodiments, the combination plate wells 303 each comprise a respective mating collar 312 that extends away from a top surface of the well plate 309, thereby extending the walls of the corresponding combination plate well 303 from the top surface of the well plate 309. The mating collars 312 of the wells 303 of the combination microplate 300 are sized and shaped to fit within, or otherwise mate with, the well orifices of the assay microplate 500. In preferred embodiment, the mating collars 312 are sized and fit to create an interference fit with the corresponding perfusable units 503 of the assay microplate 500 to facilitate a leak-free transfer of the one or more cells and any associated liquid that is included in the respective combination plate well 303.

According to various embodiments, the combination microplate 300 further comprises an alignment guide 115*b* and an alignment receiving aperture 118*b* to facilitate an aligned placement of the starter microplate 100 over the combination microplate 300 when mating the starter microplate 100 with the combination microplate 300. In addition, the alignment guide 115 and alignment receiving aperture 118*b* are further used to facilitate an aligned placement of the combination microplate 300 over the assay microplate 500 when mating the combination microplate 300 with the assay microplate 500. In particular, the alignment guide 115 may be sized and shaped to align with and engage with a receiving aperture 118 that is included on the starter microplate 100 and/or the assay microplate 300.

Figure 5:
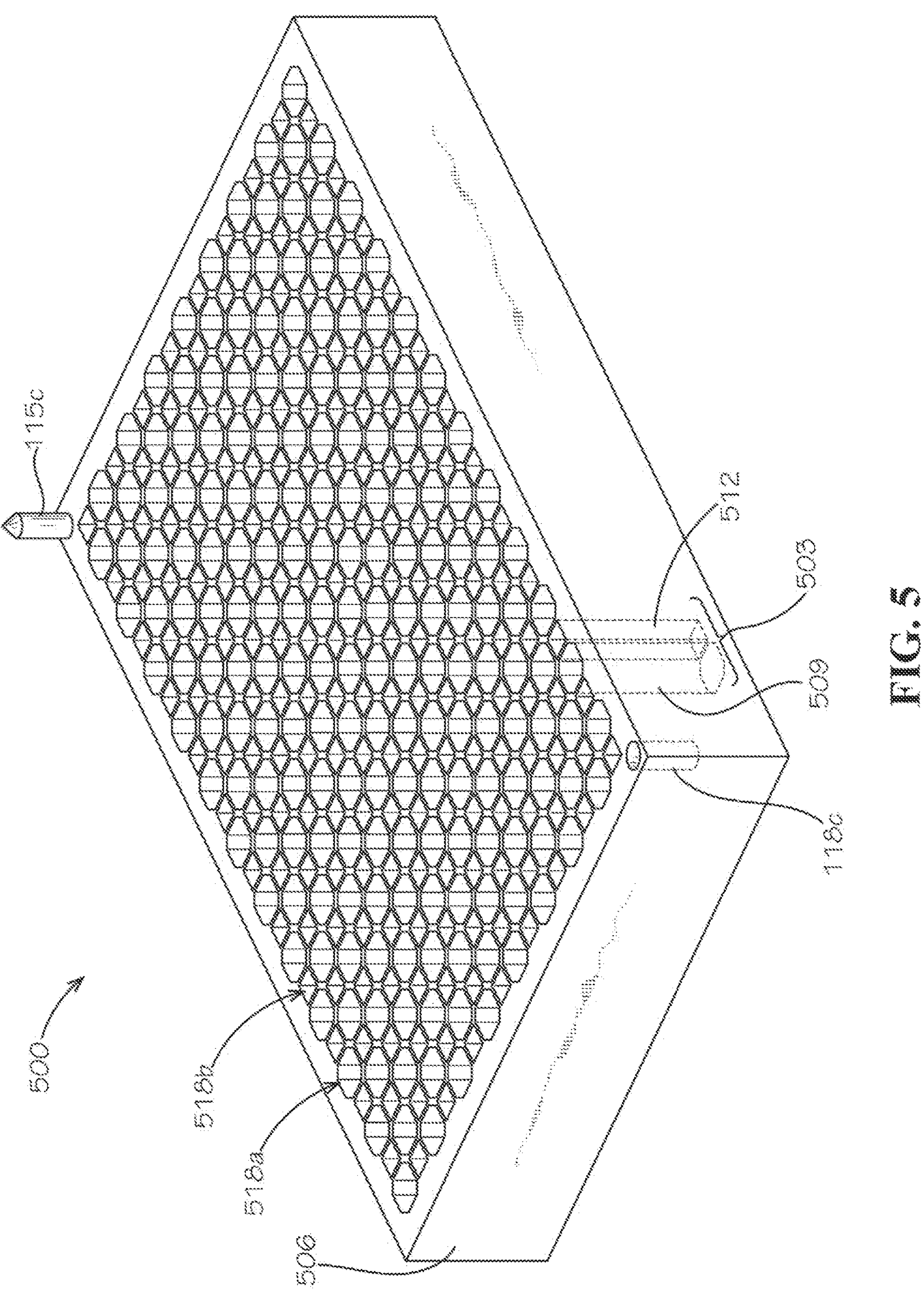
FIG. 5 illustrates an example of a perspective view of an assay microplate in accordance with various embodiments of the present disclosure.
Figure 6:
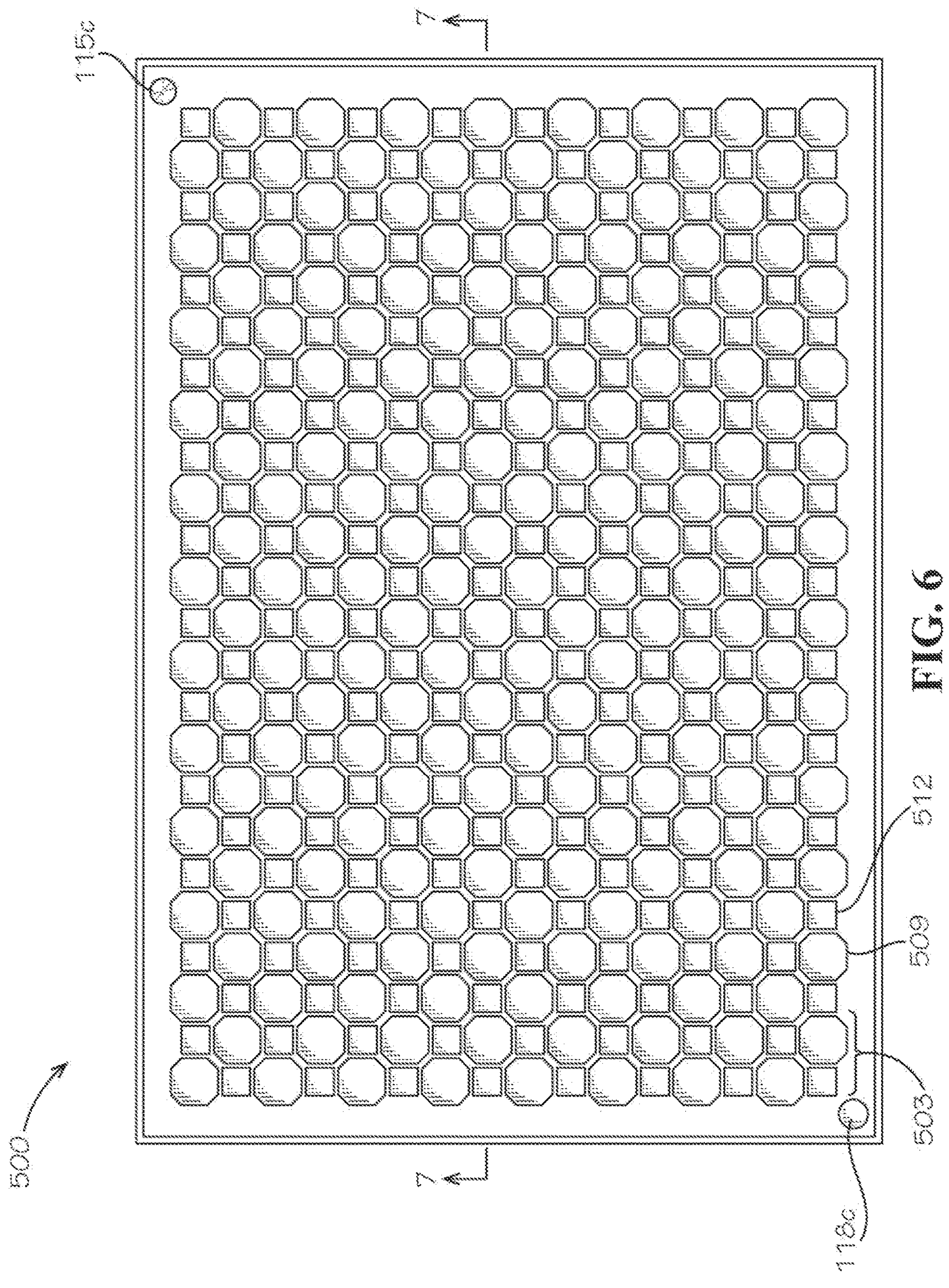
FIG. 6 illustrates an example of a top view of the assay microplate of FIG. 5 in accordance with various examples of the present disclosure.

As depicted in FIG. 5, the assay microplate 500 further comprises an alignment guide 115*c* and an alignment receiving aperture 118*c*. It should be noted that although the placement of the alignment guides 115 and alignment apertures 118 of the combination microplate 300 and the assay microplate 500 are illustrated in FIGS. 5 and 6 as being in opposite corners of the microplates 300, 500 to allow proper engagement when the combination microplate 300 is inverted and placed over the assay microplate 500, the positioning of the alignment guides 115 and receiving apertures 118 are not limited to the positions illustrated in the FIGS. 3 and 5.

It should be noted that although the present disclosure discusses a starter microplate 100 and a combination microplate 300, the need to use the starter microplate 100 may be optional based on the given application. For example, if a given application does not require the combination of different types of cells, the initial growth of the cells can occur using the combination microplate 300 without the additional need for growth and/or culturing cells in the starter microplate 100. In another example, if culture is started using embryoid bodies from another source, the use of the starter plate can be optional.

Assay Plate

Turning now to FIG. 5, shown is a perspective view of an example assay microplate 500 in accordance with various embodiments of the present disclosure. FIG. 6 illustrates an example of a top view of the assay microplate 500 of FIG. 5 in accordance with various examples of the present disclosure. As can be appreciated, the assay microplate 500 corresponds to a culturing and assay microplate for growing, culturing, monitoring, and assaying embryoid bodies, fused embryoid bodies, spheroids, organoids, or other multi-cellular bodies. According to various examples, the assay microplate 500 is designed to support and grow organoids that are sized in the range of 25 micrometers to greater than about 100 micrometers in diameter.

As shown in FIG. 5, the assay microplate 500 comprises a well plate 506 having a plurality of perfusable units 503 for growing, culturing, monitoring and assaying embryoid bodies, fused embryoid bodies, spheroids, organoids, and/or other multi-cellular bodies. In various examples, the well plate 506 comprises a planar material having a top surface, a bottom surface, and a thickness corresponding to a desired well height. The components of the well plate 506 may be formed of any suitable material by any suitable procedures. In exemplary embodiments, the well plate 506 may be formed of polymer, such as a transparent polymer, and/or other material as can be appreciated. For example, the polymer may comprise polystyrene, polypropylene, poly (methyl methacrylate), cyclic olefin polymer, cyclic olefin copolymer, and/or other polymer as can be appreciated. The well plate 506 may have no removable/moving parts and/or may be formed as a single piece, such as by injection molding, such that all of the structures (e.g., wells) of the well plate 506 are formed integrally with one another.

According to various embodiments, a perfusable unit 503 comprises a culture well 509 and a supply well 512 that are fluidly connected with one another via at least one channel 515 that is sized and shape to facilitate a gravitational flow of liquid (e.g., feeding medium) between the culture well 509 and the supply well 512 in response to a tilting of the assay microplate 500. Exchanging the media between the culture well 509 and the supply well 512 removes toxic by-products and supplies the growing organoid or other tissue cultures with fresh nutrients.

According to various embodiments, the culture well 509 is sized and shaped to support the deposited embryoid bodes that may be embedded in hydrogel that is introduced into the culture well 509. For example, the culture well 509 may be considered a culture well that is used to grow the embryoid bodies, as can be appreciated. According to various embodiments and dependent upon a number of wells one the assay plate 500, the size of the culture well 509 can be up to 6 millimeters (mm) in one dimension, up to 15 mm in the one dimension, and/or other size as can be appreciated. In addition, the depth of the culture well 509 and the supply well 512 is specified such that the assay microplate 500 may be tilted to allow fluid exchange within the perfusable units 503 without spilling the fluid out of the respective culture well 509 or supply well 512 of each the perfusable units 503.

The supply well 512 may be used to supply feeding media and/or other nutrients that can be used to feed the growing organoids positioned in the culture well 509. In addition, the supply well 512 can be used to harvest supernatant from the organoids, as can be appreciated. For example, the supply well 512 can be considered a supply well that comprises the feeding media and/or other nutrients that may be used by the growing organoid in the culture well 509. The supply well 512 is sized and shape to hold fluid that can be exchanged with the culture well 509 according to various embodiments of the present disclosure. According to various embodiments and dependent upon a number of wells one the assay plate 500, the size of the supply well 512 can be up to 6 millimeters (mm) in a given dimension, up to 15 mm in the given dimension, and/or other size as can be appreciated. It should be noted that in some examples, the supply well 512 may provide the environment for growing and culturing the organoids and/or other multi-cellular bodies and the culture well 509 may be used as the supply well for supplying nutrients to the environment within the supply well 512.

According to various embodiments, the size and shape of the culture well 509 and the supply well 512 may differ from one another. For example, in some examples, the culture well 509 is larger (in a dimension, for example diameter or volume) than the supply well 512. In other examples, the supply well 512 is larger than the culture well 509. In some examples, the culture well 509 comprises a shape that differs from a shape of the supply well 512. It should be noted that although the examples of the culture wells 509 and the supply wells 512 of the present disclosure illustrate the culture well 509 as being octagon-shaped and the supply well 512 as being square-shaped, the sizes and shapes of the culture well 509 and supply well 512 are not limited to the sizes and shapes shown in the example figures.

The perfusable units 503 are preferably arrayed in columns and rows as depicted in FIGS. 5 and 6. In various embodiments, the assay microplate 500 comprises a 384 well-style plate comprising one-hundred and ninety-two (192) culture wells 509 for organoids or other tissue cultures as can be appreciated. However, it should be noted that the assay microplate 500 is not limited to a 384 well style plate and can be organized as a strip, or other type of configuration as can be appreciated.

According to various embodiments, the culture well 509 is defined by a culture well orifice 518*a* formed by one or more walls that extend from a top of the well plate 506 to a bottom surface of the culture well 509. Similarly, the supply well 512 is defined by a supply well orifice 518*b* defined by one or more walls that extend from the top surface of the well plate 506 to a bottom surface of the supply well 512. In various embodiments, the culture well 509 is positioned adjacent to a supply well 512 such that the culture well 509 and the supply well 512 share a sidewall 519 or at least a portion of a wall shared between the culture well 509 or the supply well 512. In various examples, the shared sidewall 519 of the culture well 509 and the supply well 512 (or the portion of the wall shared between the culture well 509 and the supply well 512) does not extend the entire length from the top surface to the bottom surface of the well plate 506.

According to various embodiments, the assay microplate 500 further comprises a bottom layer sheet 521 disposed on an underside of the well plate 506. The bottom layer sheet 521 is attached to the underside of the well plate 506 forming the bottom surfaces of the culture wells 509 and the supply wells 512. In various examples, the bottom layer sheet 521 comprises a viewing window that is optically transparent to allow for imaging of organoids or other tissue cultures being cultured in the assay microplate 500, as can be appreciated. The viewing window can be a window that is suitable for microscopic observation, whether brightfield, phase-contrast, fluorescent, confocal, two-photon, or other microscopic imaging modalities as known in the art.

In various examples, the bottom layer sheet 521 can comprise a gas permeable sheet that is configured to increase an oxygen supply for the growing organoids in the assay microplate 500. The gas permeable sheet can be formed of a material comprising polytetrafluoroethylene (PTFE), PEFP, Polyimide, and/or other material as can be appreciated. According to various examples, the gas permeable sheet can have a thickness of about 5-30 microns. According to various examples, the gas permeable sheet may comprise a plurality of pores. In other examples, the gas permeable sheet may allow molecules to pass by diffusion. Alternatively, the gas permeable sheet may comprise some other thickness, pore diameter, and pore density.

According to various embodiments, the bottom layer sheet 521 is attached to the underside of the sidewalls of the culture wells 509 and supply wells 512 that extend from the top surface to the bottom surface of the well plate 506. According to various examples, the bottom layer sheet 521 is attached to the well plate 506 via thermocoupling, an adhesive, and/or other method of attachment as can be appreciated.

According to various embodiments, the fluid connection between the culture wells 509 and the adjacent supply wells 512 and the ability to provide a continual gravitational flow of fluid via the tilting of the assay microplate 500 allows for advance feeding of the organoids or other multi-cellular bodies. In various examples, feeding media or other nutrients may be introduced into the supply well 512 and ultimately introduced into the culture well 509 via the channel 515. In various embodiments, liquid can be removed from one of the wells (e.g., supply well 512) by aspiration without disturbing the environment in the well of interest. In various examples, the fluid connection of the wells of the perfusable units 503 further allows for observation of the tissue cultures in a hydrogel that may be in contact with two different liquids to create a gradient of concentrations within the hydrogel as can be appreciated.

Figure 7:
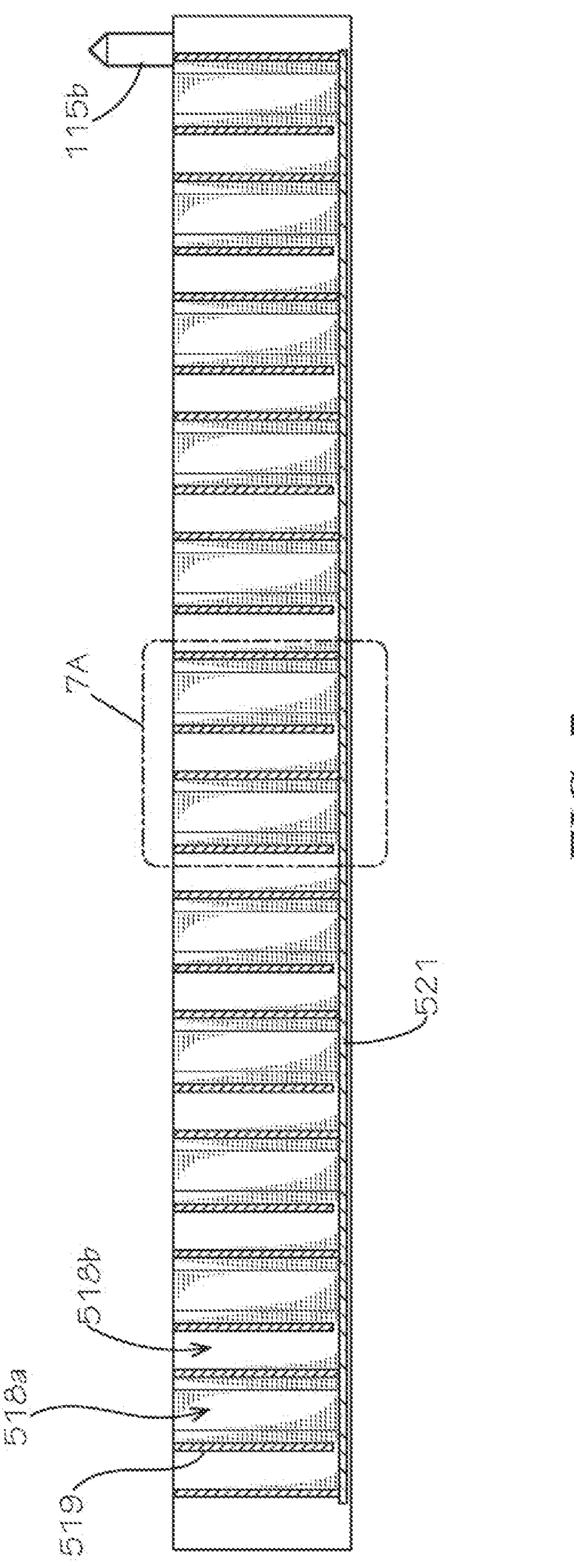
FIGS. 7 and 7A illustrate a cross sectional view of an embodiment of the assay microplate of FIG. 5 showing perfusable units having supply wells being fluidly connected to culture wells via a channel in accordance with various embodiments of the present disclosure.
Figure 7A:
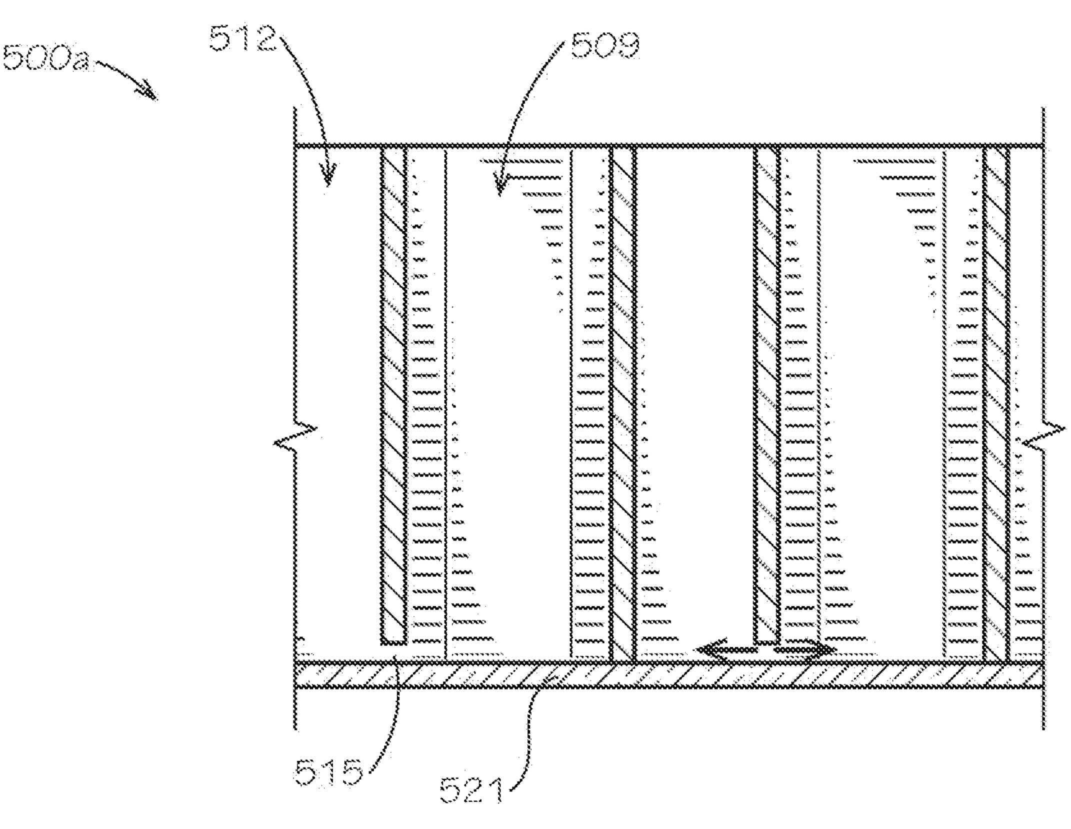

Turning now to FIGS. 7-10, shown are example views of an assay microplate 500*a* according to various embodiments of the present disclosure. In particular, FIG. 7 illustrates a cross-sectional view of the assay microplate 500*a* illustrating a channel 515 that fluidly connects the culture well 509 with the supply well 512. FIG. 7A illustrates a zoomed-in view of a section of the cross-sectional view of the assay microplate 500*a* of FIG. 7. As shown in FIGS. 7-10, the shared sidewall 519 of the culture well 509 and the supply well 512 is shorter in length than the remaining sidewalls of the culture well 509 and the supply well 512. In particular, the shared sidewall 519 does not extend to the bottom surface of the culture well 509 and supply well 512 that is formed by the bottom layer sheet 521. As such, a gap forming the channel 515 is present between the end of the shared sidewall 519 and the bottom layer sheet 521. The gap is sized to prevent organoids from being able to migrate through the channel 515 into the supply well 512. In various non-limiting examples, the gap can be about 25 μm to about 4 mm high.

Figure 8:
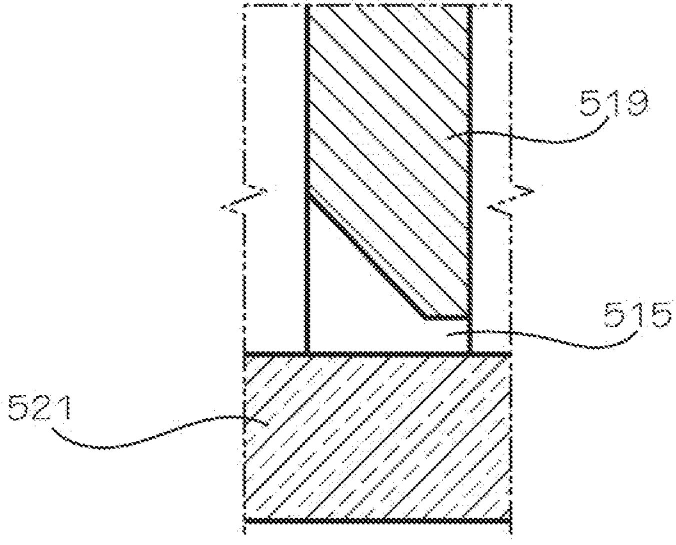
FIG. 8 illustrates an example of a detailed view of a channel of FIG. 7 connecting a supply well with a culture well in accordance with various embodiments of the present disclosure.

FIG. 8 illustrates a detailed view of an example of the channel 515 formed by the gap between the end of the shared sidewall 519 and the top surface of the bottom layer sheet 521. In various examples, an end of the shared sidewall 519 can comprise a sloped surface between the supply well 512 and the culture well 509. As discussed, the channel 515 provides for an opening between the connected wells to allow for a perfusive flow of media to provide nutrients to the tissue cultures in the culture well 509 from the media in the supply well 512 and to remove potentially toxic by-products from the culture well 509.

Figure 9:
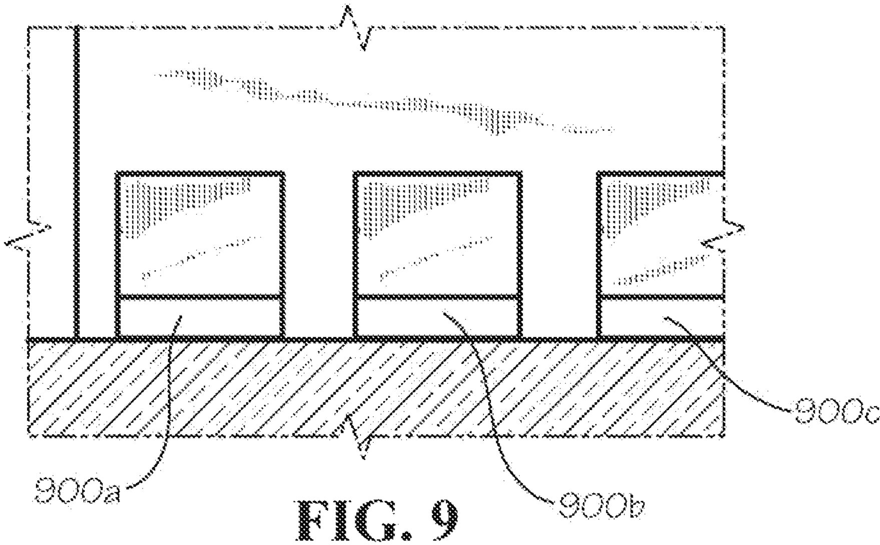
FIG. 9 illustrates an example channel of FIG. 7 having shallow microchannels in accordance with various embodiments of the present disclosure.
Figure 10:
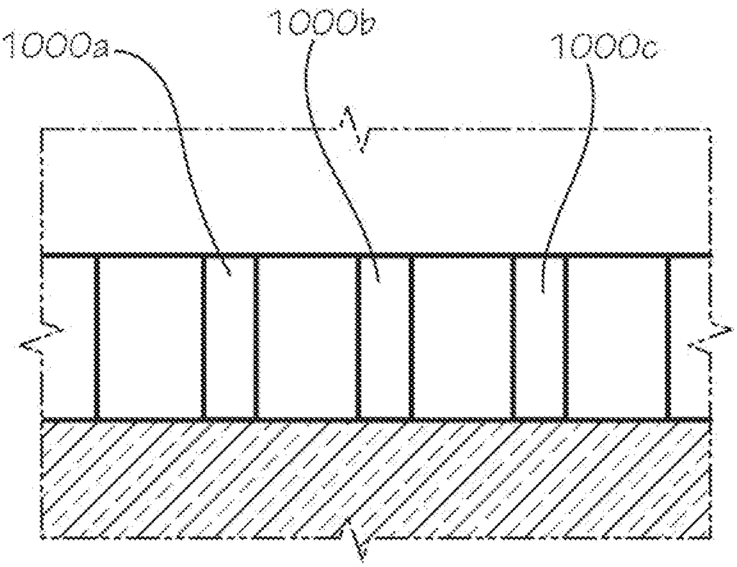
FIG. 10 illustrates an example channel of FIG. 7 having vertical microchannels in accordance with various embodiments of the present disclosure.

According to various examples, the channel 515 between the supply well 512 and the culture well 509 may comprise microchannels. FIGS. 9 and 10 illustrate example configurations of microchannels according to various embodiments. In particular, FIG. 9 illustrates an example of a cross-sectional view of an example channel 515 having shallow microchannels 900 (e.g., 900*a*, 900*b*, 900*c*) wherein the width of each shallow microchannel 900 is greater than a height of each shallow microchannel 900. According to various embodiments, the width of the shallow microchannels 900 can be in the range of 25 μm to about 200 μm wide. In various non-limiting examples, the height of the shallow microchannels 900 can in the range of about 25 μm to about 200 μm high. In other non-limiting examples, the height of the shallow microchannels 900 may extend a height of the corresponding wall(s) of the supply well 512 and the culture well 509. In some examples, hydrogel that comprises one or more cells may be is introduced into the culture wells 509 and may fill a bottom of a well and flow into a well connection or shallow microchannel 900 as can be appreciated.

Turning now to FIG. 10, shown is an example of a cross-sectional view of an example channel 515 having vertical microchannels 1000 (e.g., 1000*a*, 1000*b*, 1000*c*) having a height that is greater than a width of each vertical microchannel 1000. The channel 515 is split up into multiple microchannels 1000 by separation walls. According to various embodiments, the height of the vertical microchannels 1000 can be up to about 100 μm high. The width of the vertical microchannels 1000 can be up to about 50 μm wide. In some examples, as hydrogel that comprises one or more cells is introduced into a given culture well 509, the hydrogel may fill a well connection or vertical microchannel 1000, as can be appreciated.

Figures 11, 11A:
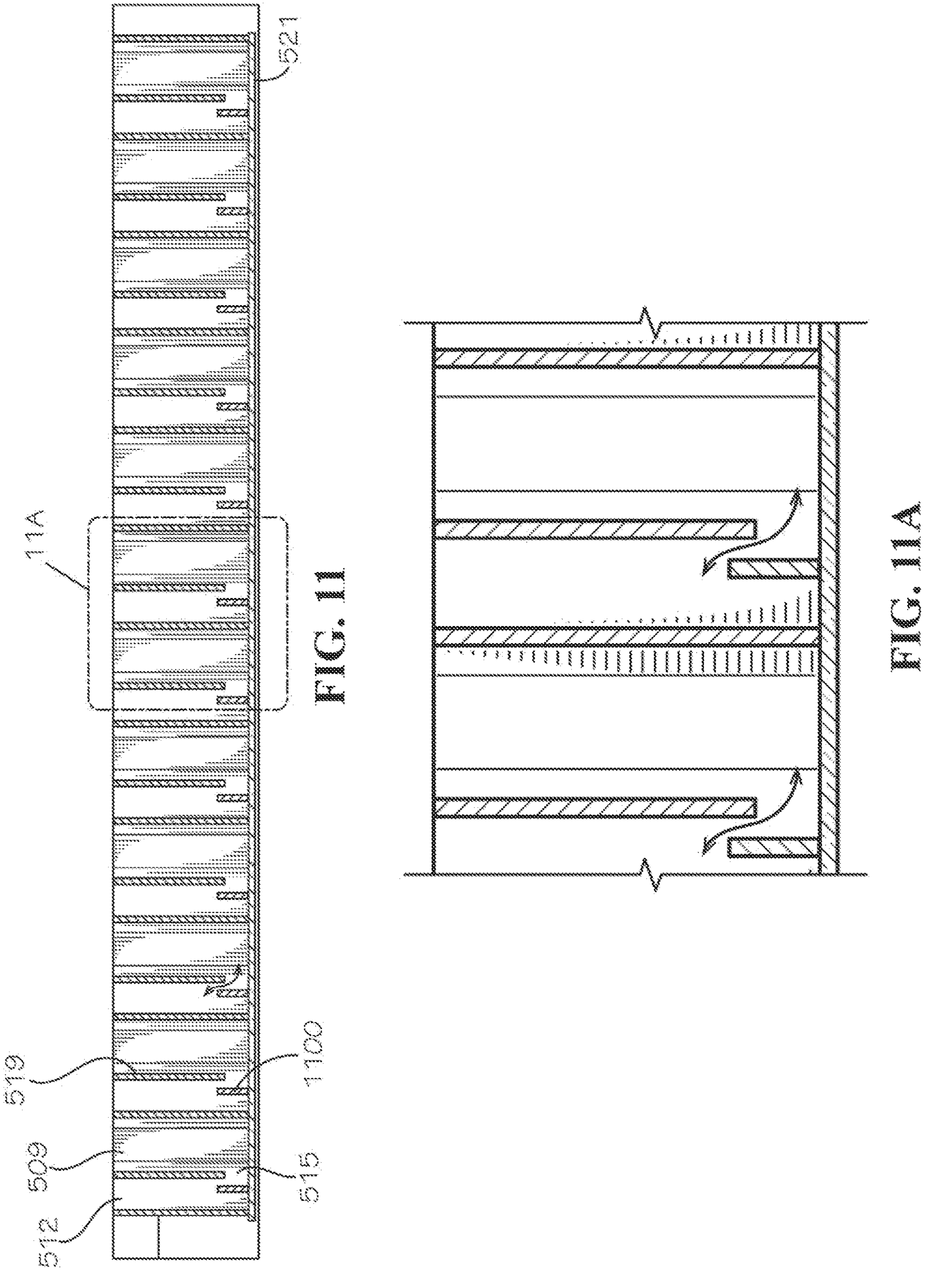
FIGS. 11 and 11A illustrate a cross sectional view of another embodiment of the assay microplate of FIG. 5 illustrating a channel that fluidly connects culture wells with supply wells in accordance with various embodiments of present disclosure.

Moving on to FIGS. 11-14, shown are example views of an assay microplate 500*b* according to various embodiments of the present disclosure. In particular, FIG. 11 illustrates a cross sectional view of the assay microplate 500*b* illustrating a channel 515 that fluidly connects the culture well 509 with the supply well 512. The assay microplate 500*b* of FIG. 11 illustrates an alternative channel configuration from that of the assay microplate 500*a* of FIG. 7.

Figure 13:
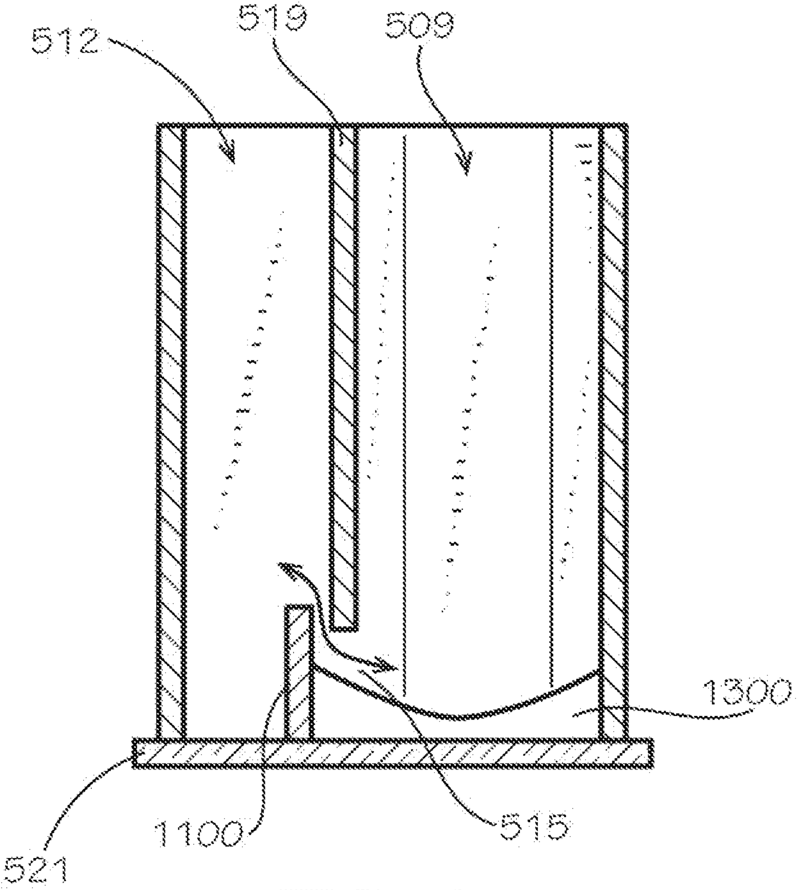
FIG. 13 illustrates an example of a cross sectional view of a perfusable unit of the assay microplate of FIG. 11 with hydrogel deposited in the bottom of the culture well and extending into the supply well in accordance with various embodiments of the present disclosure.

As shown in FIGS. 11 and 13, the shared sidewall 519 of the culture well 509 and the supply well 512 is shorter than the remaining sidewalls of the culture well 509 and the supply well 512. In particular, the shared sidewall 519 does not extend to the bottom surface of the culture well 509 and supply well 512 that is formed by the bottom layer sheet 521. As such, a gap forming the channel 515 exists between the end of the shared sidewall 519 and the bottom layer sheet 521. The gap is sized to prevent organoids from being able to migrate into the supply well 512. In various non-limiting examples, the gap can be about 25 μm to about 200 μm high. In other non-limiting examples, the height of the gap may extend a height of the corresponding wall(s) of the supply well 512 and the culture well 509.

In contrast to the assay microplate 500*a* of FIG. 7, the assay microplate 500*b* of FIG. 11 includes a barrier wall 1100 that is parallel to the shared sidewall 519 that extends perpendicularly away from the bottom layer sheet 521 towards the top surface of the well plate 506. The channel 515 of the assay microplate 500*b* that provides a fluid connection between the culture well 509 and the supply well 512 is formed by the gap between the shared sidewall 519 and the bottom surface of the culture well 509 and supply well 512, as well as the space formed between the barrier wall 1100 and the shared sidewall 519. As shown in FIG. 13, in various embodiments, hydrogel 1300 that is deposited into the culture well 509 can flow into a portion of the supply well 512 up to the barrier wall 1100, thereby preventing the hydrogel 1300 from being deposited fully into the supply well 512.

FIG. 11A illustrates an example of a zoomed-in view of the assay microplate 500*b* of FIG. 11 and shows and example of the gravitational flow of liquid between the culture well 509 and the supply well 512 in response to a tilting of the assay microplate 500*b* as can be appreciated. In particular, liquid that is introduced into the supply well 512 can flow over the barrier wall 1100 and into the channel 515 formed from the shared sidewall 519 and the bottom layer sheet 521. Likewise, liquid that is in the culture well 509 can flow through the channel 515 and over the barrier wall 1100 into the supply well 512, as can be appreciated. It should be noted that while the barrier wall 1100 is illustrated in FIGS. 11-13 as being positioned on the supply well side of the shared sidewall 519, in various embodiments, the barrier wall 1100 may be positioned on the culture well side of the shared sidewall 519.

Figure 12:
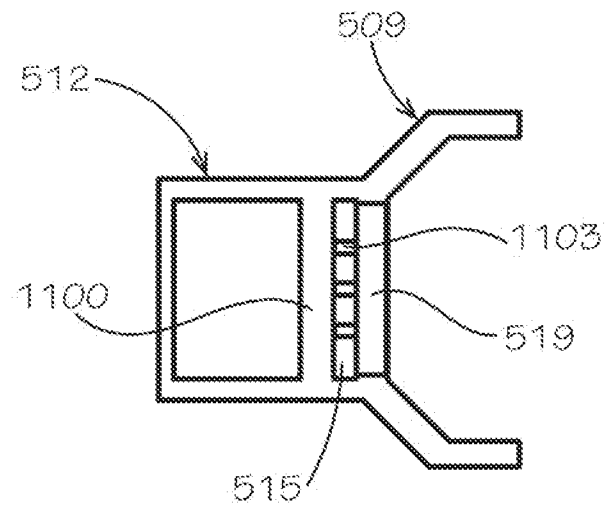
FIG. 12 illustrates an example of a top view of a perfusable unit of the assay microplate of FIG. 11 in accordance with various embodiments of the present disclosure.

FIG. 12 illustrates an example of a top view of a perfusable unit 503 of the assay microplate 500*b*. As discussed in FIGS. 9 and 10, the channel 515 formed in the assay microplate 500 may comprise microchannels. In the example of FIG. 12, the portion of the channel 515 that is formed by the space between the barrier wall 1100 and the shared sidewall 519 may comprise microchannels 1103 that can be used to prevent the migration of embryoid bodies into the adjacent well. In some examples, the portion of the channel 515 formed by the gap between the shared sidewall 519 and the bottom layer sheet 521 may comprises shallow microchannels 900 or vertical microchannels 1000, as can be appreciated.

Figure 14:
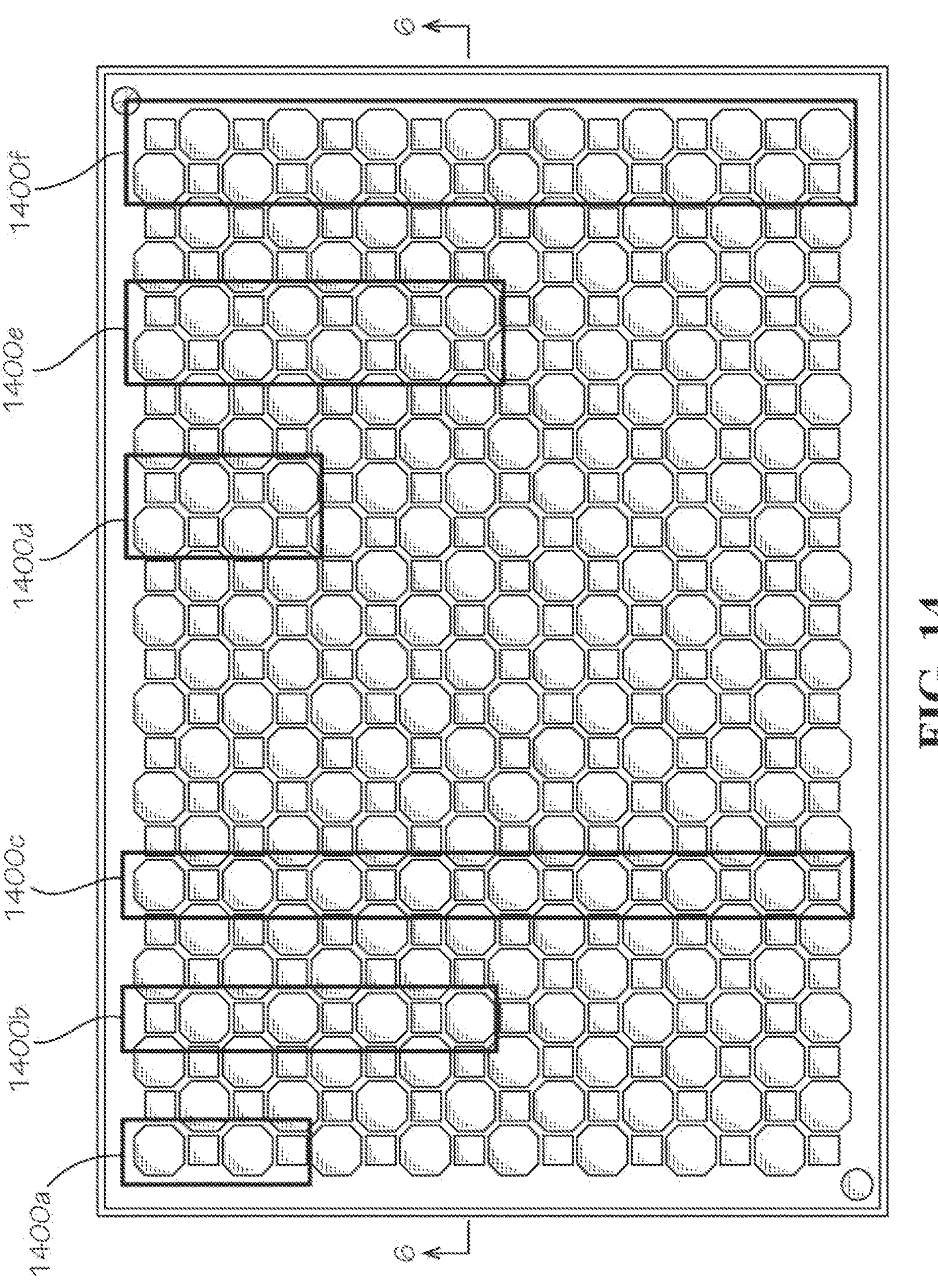
FIG. 14 illustrates an example of a top view of the assay microplate of FIG. 5 showing different chip configurations in accordance with various embodiments of the present disclosure.

Turning now to FIG. 14, shown is another example of a top view of an assay microplate 500 as can be appreciated. In particular, FIG. 14 illustrates example configurations 1400 (e.g., 1400*a*, 1400*b*, 1400*c*, 1400*d*, 1400*e*, 1400*f*) where multiple perfusable units 503 (e.g., 4, 6, 8, 10, 12, etc.) may be fluidly connected to allow the exchange of media via a gravitational flow between multiple perfusable units 503. In particular, FIG. 14 illustrates how the assay microplate 500 can be configured to provide multiple different configurations where liquid may be exchanged from multiple different organoids or tissue cultures that are embedded in environments within the different perfusable units 503.

For example, in some embodiments, each supply well 512 and culture well 509 in a given configuration 1400 may comprise two or more channels 515 on two or more sidewalls to allow fluid to flow throughout the different perfusable units 503. In other words, the different perfusable units 503 may be fluidly connected to one another via channels 515 between supply wells 512 and culture wells 509 of adjacent perfusable units 503. As such, if a first culture well 509 of a perfusable unit 503 in configuration having two connected perfusable units 503 (e.g., configuration 1400*a*) comprises a first type of embryoid body and a second culture well 509 of a perfusable unit 503 in the same configuration comprises a second type of embryoid body, the same fluid is exchanged between both embryoid bodies.

Figure 15:
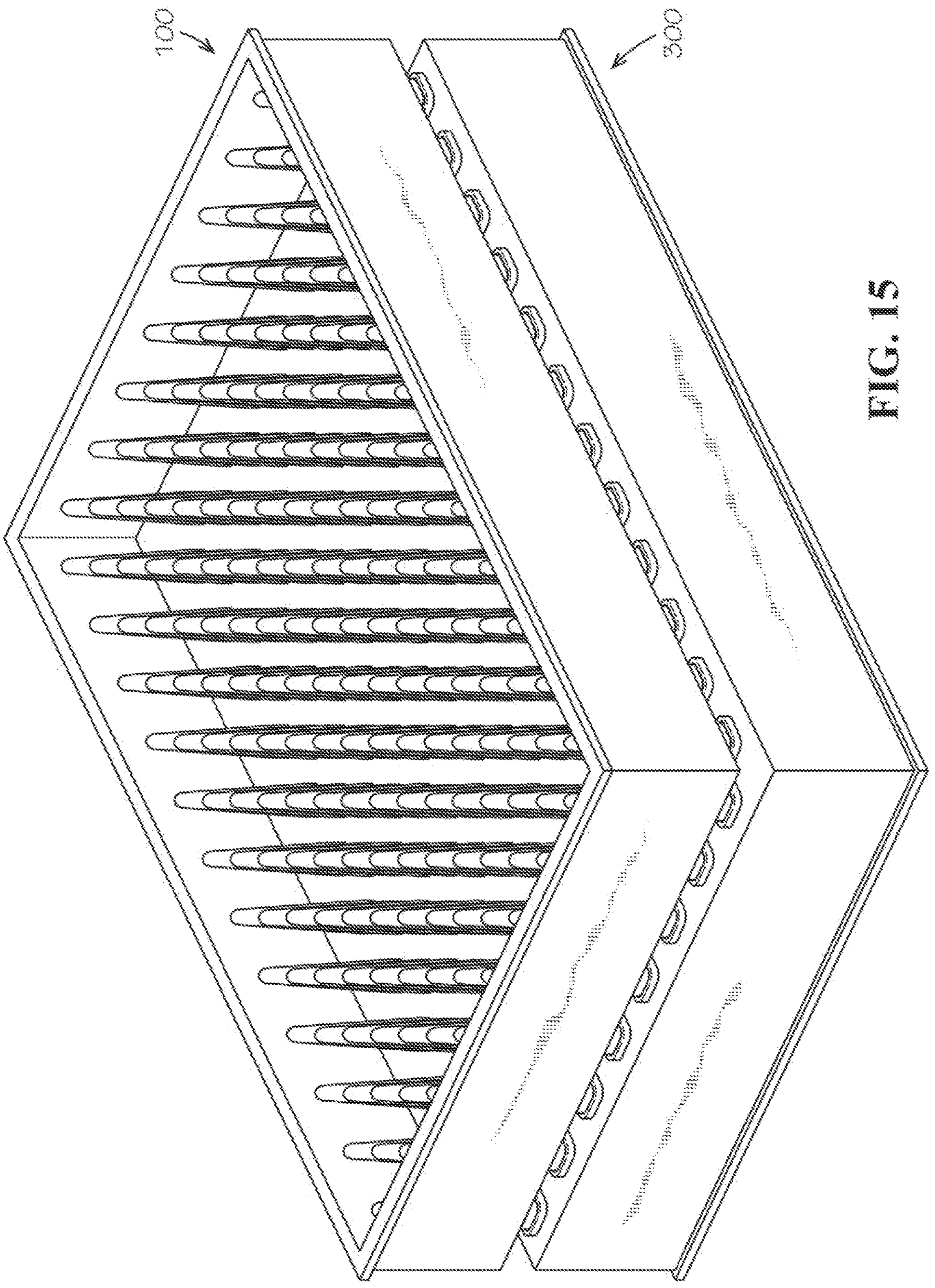
FIG. 15 illustrates an example of a perspective view of the starter microplate of FIG. 1 mated with the combination microplate of FIG. 3 in accordance with various embodiments of the present disclosure.
Figure 16:
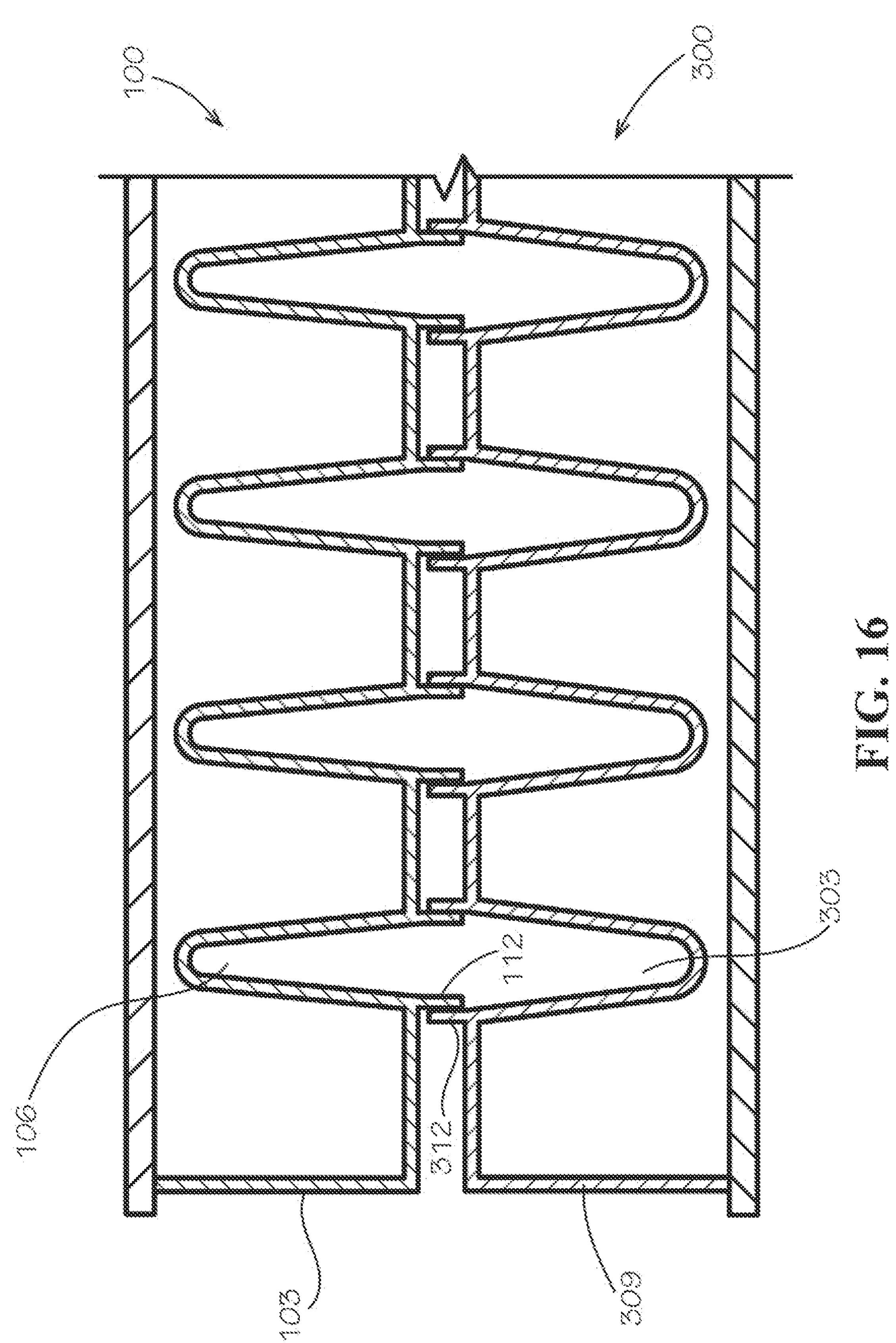
FIG. 16 illustrates an example of a cross sectional view of starter microplate of FIG. 1 mated with the combination microplate of FIG. 3 in accordance with various embodiments of the present disclosure.

Referring next to FIGS. 15-18B, shown are examples of how the different microplates 100, 300, 500 of the system of microplates can be interconnected with one another in order to transfer one or more cells from wells in one microplate into wells of another microplate. FIG. 15 illustrates a perspective view of the starter microplate 100 mated with the combination microplate 300, and FIG. 16 illustrates a cross sectional view of the starter microplate 100 mated with the combination microplate 300. As discussed with regard to FIGS. 1 and 3, in one embodiment a kit or system of microplates includes the starter microplate 100 that is compatible with a combination microplate 300 (FIG. 3) to facilitate the transfer of one or more cells, embryoids, organoids, or other biological matter from the starter microplate 100 to the combination microplate 300. In various embodiments, a positioning of the culture wells 509 (or supply wells 512) of the perfusable unit 503 on the microplate 500 mirror a positioning of the combination plate wells 303 on the combination microplate 300, thereby allowing respective ones of the combination plate wells 303 to mate with corresponding wells of culture wells 509 (or supply wells 512) of the perfusable unit 503. As shown in FIGS. 15 and 16, the starter microplate 100 is mated with the combination microplate 300 by inserting the mating collars 112 of the starter microplate 100 into corresponding combination plate wells 303 of the combination plate 300.

For example, in some embodiments, the starter microplate 100 may be inverted and positioned over the combination microplate 300 to allow for the starter plate wells 106 of the starter microplate 100 to engage with or otherwise interconnect with corresponding combination plate wells 303 of the combination microplate 300.

Figure 25:
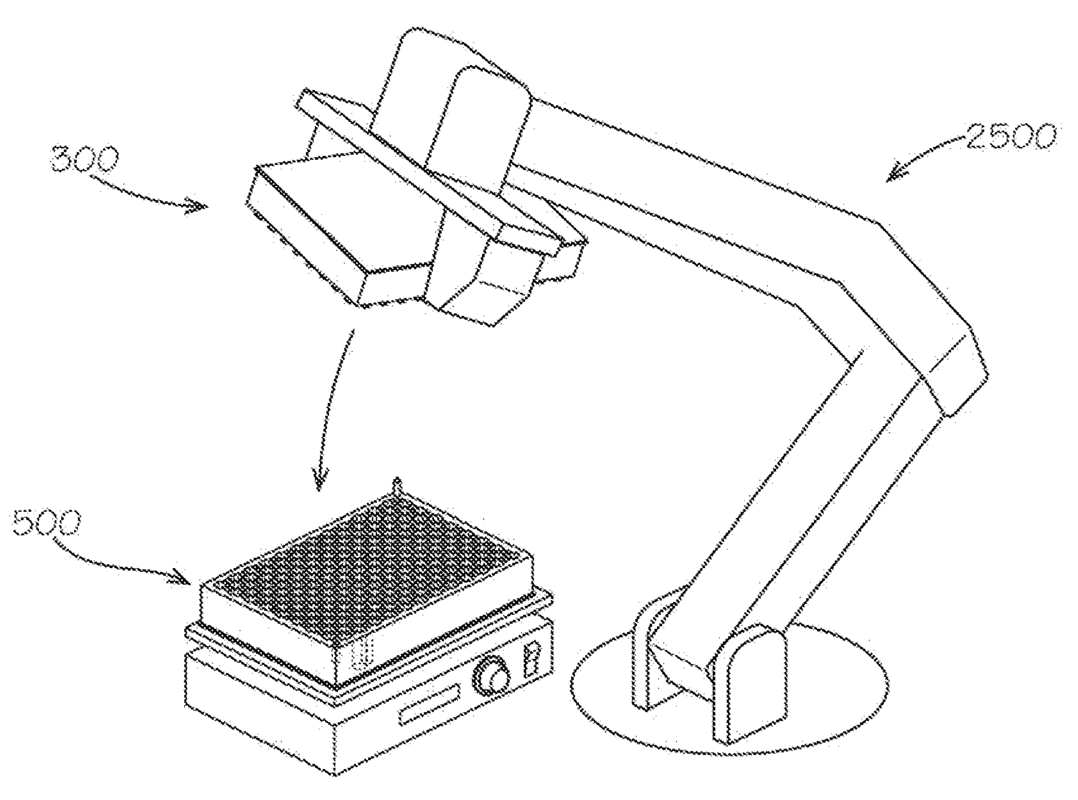
FIG. 25 illustrates an example of the combination plate of FIG. 3 being mated with the assay microplate of FIG. 5 using a robotic apparatus in accordance with various embodiments of the present disclosure.

In particular, the mating collar 112 of the starter microplate 100 are disposed within and engage with the mating collar 312 of the combination microplate 300. In various examples, the mating collar 112 of the starter microplate 100 engage with the mating collar 312 of the combination microplate 300 to create an interference fit that facilitates a leak-free transfer of the one or more cells and any associated liquid from wells 106 of the starter microplate 100 into corresponding wells 106 of the combination microplate. The engagement of the starter microplate 100 and the combination microplate 300 can be performed manually or through the use of automated systems, subsystems, or components, such as, for example, a robotic apparatus 2500 as shown in FIG. 25.

Figure 17:
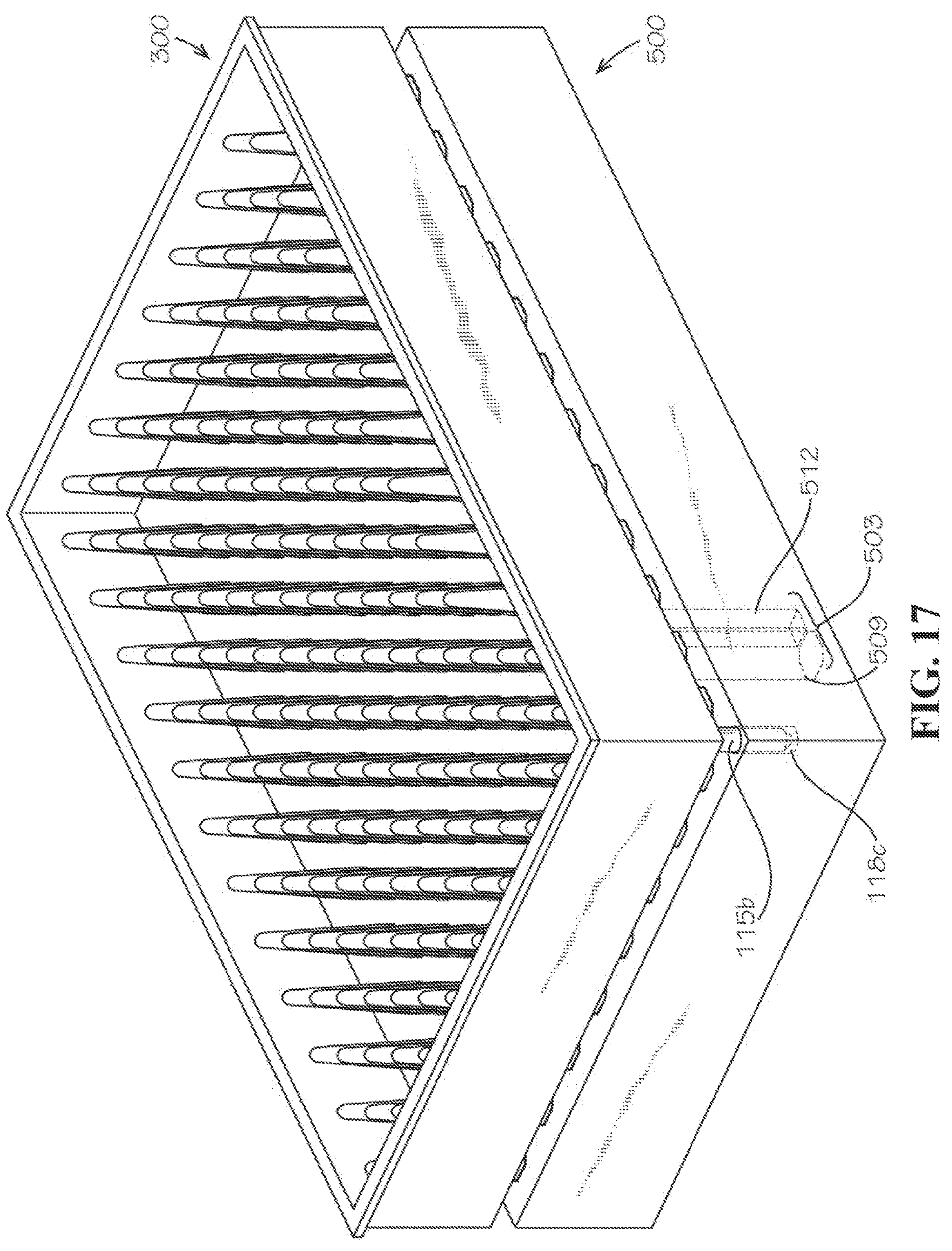
FIG. 17 illustrates an example of a perspective view of the combination microplate of FIG. 3 mated with the assay microplate of FIG. 5 in accordance with various embodiments of the present disclosure.
Figure 18A:
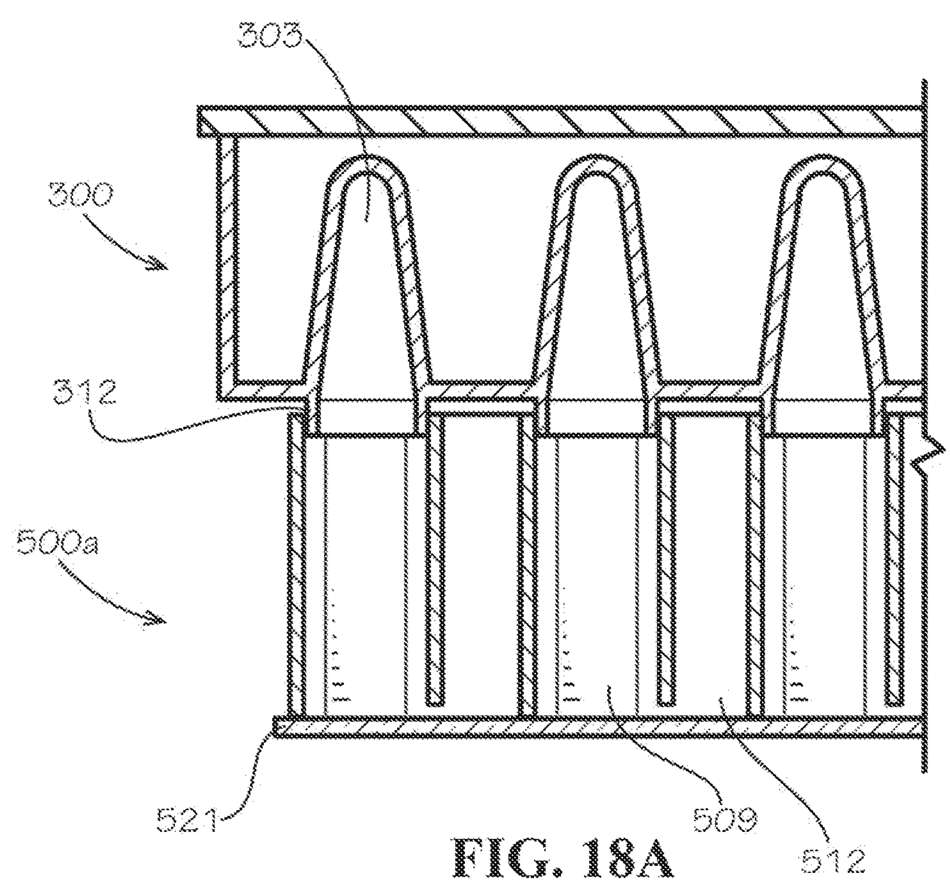
FIG. 18A illustrates an example of a cross sectional view of the combination plate of FIG. 3 mated with the assay microplate of FIG. 7 in accordance with various embodiments of the present disclosure.
Figure 18B:
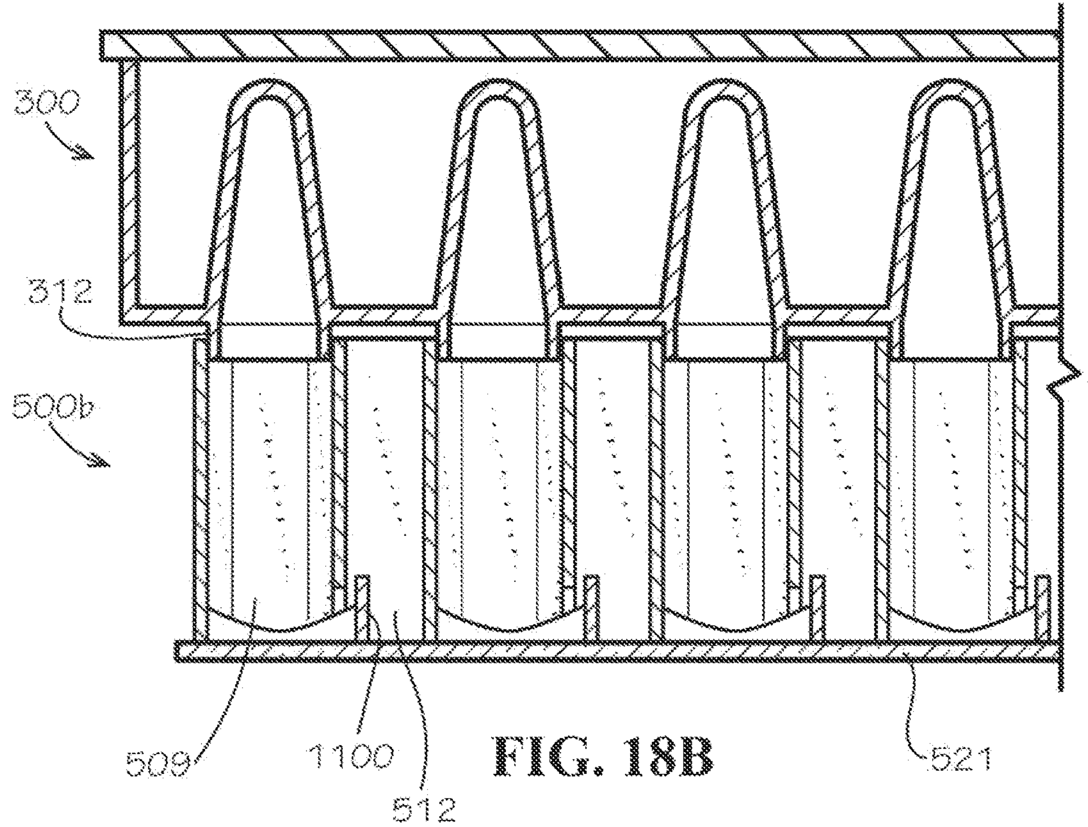
FIG. 18B illustrates an example of a cross sectional view of the combination plate of FIG. 3 mated with the assay microplate of FIG. 11 in accordance with various embodiments of the present disclosure.

FIG. 17 illustrates a perspective view of the combination microplate 300 mated with the assay microplate 500. FIG. 18A illustrates a cross sectional view of the combination microplate 300 mated with the assay microplate 500*a* and FIG. 18B illustrates a cross sectional view of the combination microplate 300 mated with the assay microplate 500*b*. As discussed with regard to FIGS. 3 and 5, the combination microplate 300 is compatible with an assay microplate 500 (FIG. 5) of the system of microplates to facilitate the transfer of one or more cells from the combination microplate 300 to the assay microplate 500.

As shown in FIGS. 17-18B, the combination microplate 300 comprises mating collar 312 extending from the combination plate wells 303 of the combination microplate 300 that are sized and shaped to engage with or otherwise interconnect with corresponding wells of a perfusable unit 503 (FIG. 5) of the assay microplate 500. According to various examples, a positioning of the culture wells 509 (or supply wells 512) of the perfusable unit 503 on the microplate 500 mirror a positioning of the combination plate wells 303 on the combination microplate 300, thereby allowing respective ones of the combination plate wells 303 to mate with corresponding wells of culture wells 509 (or supply wells 512) of the perfusable unit 503. Further, since the combination plate 300 is compatible to mate with both the starter microplate 100 and the assay microplate 500, in various embodiments, the starter plate wells 106 are positioned in a similar configuration as the culture wells 509 (or supply wells 512) of the assay microplate 500.

In various embodiments, the combination plate wells 303 each comprise a respective mating collar 312 that extends away from a top surface of the well plate 309, thereby positioning the orifice 306 of the corresponding combination plate well 303 above the top surface of the well plate 309. The mating collars 312 of the wells 303 of the combination microplate 300 are sized and shaped to fit within, or otherwise mate with, the well orifices of the assay microplate 500. In various embodiments, the mating collars 312 are sized and fit to create an interference fit with the corresponding perfusable units 503 of the assay microplate 500 to facilitate a leak-free transfer of the one or more cells and any associated liquid that is included in the respective combination plate well 303. According to various embodiments, the mating of the combination microplate 300 and the assay microplate 500 can be performed manually or through the use of automated systems, subsystems, or components, such as, for example, a robotic apparatus 2500 as shown in FIG. 25.

Figures 19, 20, 21, 22:
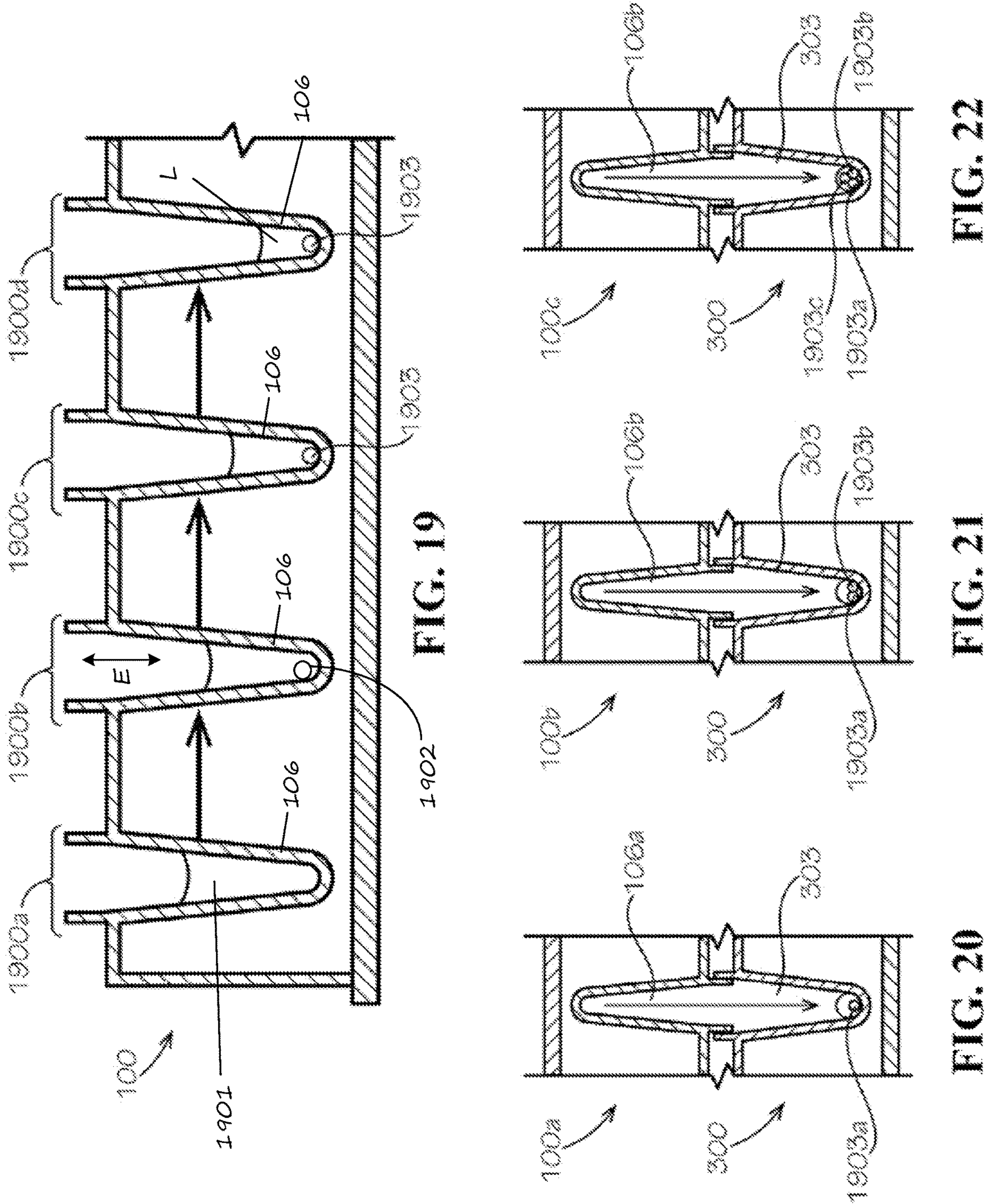
FIG. 19 illustrates an example of a time sequence associated with the creation of an embryoid body in a given well of the starter microplate of FIG. 1 in accordance with various embodiments of the present disclosure.
FIG. 20 illustrates an example cross sectional view of a starter microplate of FIG. 1 mated with the combination plate of FIG. 3 to allow for the transfer of an embryoid body in accordance with various embodiments of the present disclosure.
FIG. 21 illustrates an example cross sectional view of a starter microplate of FIG. 1 mated with the combination plate of FIG. 3 to allow for the transfer of an embryoid body into a well of the combination plate that already includes an embryoid body in accordance with various embodiments of the present disclosure.
FIG. 22 illustrates an example cross sectional view of a starter microplate of FIG. 1 mated with the combination plate of FIG. 3 to allow for the transfer of an embryoid body into a well of the combination plate that already includes multiple embryoid bodies in accordance with various embodiments of the present disclosure.

Turning now to FIGS. 19-23B, shown are examples of how the systems of microplates may be used with regard to the growth and culturing of embryoid bodies, fused embryoid bodies, spheroids, organoids, and/or other multicellular bodies, in according to various examples of the present disclosure. Starting with FIG. 19, shown is an example time sequence related to the creation of an embryoid body 1903 using the starter microplate 100 in accordance with various embodiments of the present disclosure. For illustrative purposes, FIG. 19 depicts a time increment sequence in adjacent wells 1900*a*-1900*d* of a single starter microplate 100. In laboratory applications, the stages of creation of an embryoid body 1903 in the various wells of a single starter microplate may be substantially similar (e.g., embryoid bodies may be created in substantially parallel time sequences in one or more wells of a starter microplate 100). To begin, as illustrated at the time increment 1900*a*, a cell suspension 1901 comprising one or more cells is presented in a starter well 106 of the starter microplate 100. These cells may include stem cells (e.g., pluripotent stem cells), support cells, and/or the like. The cells may be deposited in a hydrogel or hydro-scaffold by any suitable technique including bioink droplet printing, micro-contact printing, photolithography, dip pen nanolithography, and/or pipetting, among others.

As shown in time increment 1900*b*, once the cells have settled and have formed a spheroid 1902 at the bottom of the starter plate well 106, the media will be exchanged (as indicated by arrow E). The new media will contain the appropriate growth factors to create the desired embryoid body. In some examples, the media will be exchanged several times during an incubation period to create the desired embryoid body. Exemplary growth factors that may be suitable include angiopoietin, bone morphogenetic proteins (BMPs), ciliary neurotropic factor, colony stimulating factors, ephrins, epidermal growth factor, erythropoietin, fibroblast growth factors, glial-derived neurotrophic factor, hepatocyte growth factor, insulin, insulin-like growth factors, interleukins, leukemia inhibitory factor, keratinocyte growth factor, neuregulins, neurotrophins, platelet-derived growth factor, transforming growth factors, tumor necrosis factor (alpha), vascular endothelial growth factor, and/or the like.

Time increment 1900*c* illustrates the embryoid body 1903 that has been created within the starter plate well 106 following a given incubation period. Finally, as shown at time increment 1900*d*, a portion of the liquid L in the starter plate well 106 may be removed prior to transfer of the embryoid body 1903 to the combination plate 300.

FIGS. 20-22 illustrate examples of how multiple embryoid bodies 1903 (e.g., 1903*a*, 1903*b*, 1903*c*) can be introduced into the same combination plate well 303 in accordance with various embodiments of the present disclosure. Some types of applications for creating organoids require different types of embryoid bodies 1903 that are created using different growth factors. As such, the different embryoid bodies 1903 may be created in different starter microplates 100 and then transferred to a same combination plate well 303 of a combination plate by mating the different starter microplates 100*s* to the same combination plate 300.

FIG. 20 illustrates an example cross sectional view of a starter microplate 100*a* mated with the combination plate 300 to allow for the transfer of embryoid body 1903*a* created in the starter plate well 106*a* of the starter microplate 100*ba* into the combination plate well 303 of the combination plate 300. FIG. 20 illustrates the combination of the combination plate 300 on the bottom and the starter microplate 100*a* on top of the combination plate 300 to allow the embryoid body 1903 to be transferred into the combination plate well 303 of the combination microplate 300.

FIG. 21 illustrates an example cross sectional view of a starter microplate 100*b* mated with the combination plate 300 to allow for the transfer of embryoid body 1903*b* created in the starter plate well 106*b* of the starter microplate 100*b* into the combination plate well 303 of the combination plate 300. In this example, the embryoid body 1903*a* has already been transferred into the combination plate well 303 of the combination plate 300. Similar to FIG. 20, FIG. 21 illustrates the combination plate 300 on the bottom and the starter microplate 100*b* on top of the combination plate 300 to allow the embryoid body 1903*b* to be transferred into the combination plate well 303 of the combination microplate 300 that contains embryoid body 1903*a*.

FIG. 22 illustrates an example cross sectional view of a starter microplate 100*c* mated with the combination plate 300 to allow for the transfer of embryoid body 1903*c* created in the starter plate well 106*c* of the starter microplate 100*c* into the combination plate well 303 of the combination plate 300. In this example, the embryoid bodies 1903*a*, 1903*b* have already been transferred into the combination plate well 303 of the combination plate 300. FIG. 22 illustrates the combination plate 300 on the bottom and the starter microplate 100*c* on top of the combination plate 300 to allow the embryoid body 1903*c* to be transferred into the combination plate well 303 of the combination microplate 300 that contains embryoid bodies 1903*a*, 1903*b*.

In various embodiments, surface tension may hold the liquid and embryoid bodies 1903 in the starter plate wells 106 in place during the plate manipulation such that the starter plate 100 may be inverted or oriented in some other manner relative to the pull of gravity. As such, additional energy or physical agitation may be applied to the mated arrangement of plates to cause the release of the embryoid body 1903 from the starter plate well 106, thereby allowing the embryoid bodies 1903 to fall into the combination plate well 303. The additional energy or agitation may be in the form of ultrasonic impulses, mechanical impulses, spinning in a centrifuge, and/or other type of energy application as can be appreciated.

As can be appreciated, the one or more cells or embryoid bodies 1903 that are introduced into the combination plate wells 303 of the combination plate 300 may remain in the combination plate 300 during an incubation period to allow for the embryoid bodies 1903 to fuse to one another and grow as desired. During this incubation period, one or more growth factors may be introduced into the wells 303 of the combination microplate 300 in the form of a liquid medium. In some embodiments, the embryoid bodies 1903 may be embedded in a hydrogel 1300 that has been introduced into the combination plate well 303 as can be appreciated. In other examples, the embryoid bodies 1903 are embedded in a hydrogel upon transfer to the assay microplate 500. In some examples, the embryoid bodies 1903 may not be embedded in a hydrogel. Upon completion of the incubation period, the embryoid bodies 1903 can be transferred to the assay microplate 500 according to various examples of the present disclosure.

Figures 23A, 23B:
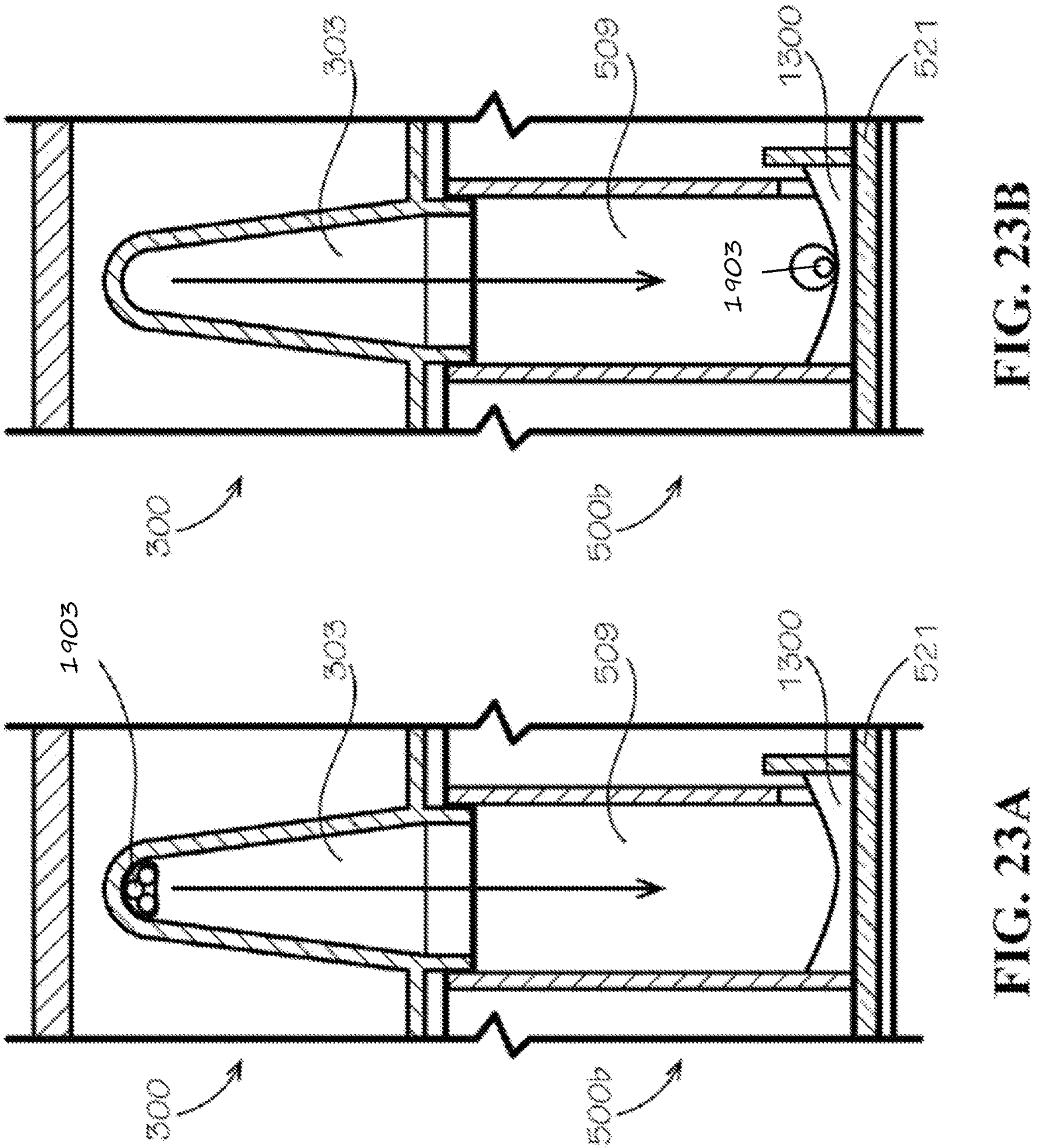
FIGS. 23A and 23B illustrate an example cross sectional view of the combination plate of FIG. 3 mated with the assay microplate of FIG. 11 where embryoid bodies are transferred from the combination plate to the assay microplate in accordance with various embodiments of the present disclosure.

FIGS. 23A and 23B illustrate an example of how the embryoid bodies 1903 can be introduced into the culture well 509 of a perfusable unit 503 of the assay microplate 500 in accordance with various embodiments of the present disclosure. As shown in FIGS. 23A and 23B, the combination plate 300 is mated with the assay microplate 500. FIG. 23A illustrates the liquid and the embryoid bodies 1903 that are disposed with the combination plate well 300. As shown in FIG. 23A, surface tension may hold the liquid (surrounding the embryoid bodies 1903) in the combination plate wells 303 in place during the plate manipulation such as when the starter plate 100 is inverted or oriented in some other manner relative to the pull of gravity. As such, additional energy or physical agitation may be applied to the mated arrangement of plates to cause the release of the embryoid bodies 1903 from the combination plate well 303, thereby allowing the embryoid bodies 1903 to fall into a corresponding culture well 509 of the assay microplate 500 and onto hydrogel 1300, as depicted in FIG. 23B. The additional energy or physical agitation may be in the form of ultrasonic impulses, mechanical impulses, spinning in a centrifuge, and/or other type of energy application as can be appreciated.

Figure 24:
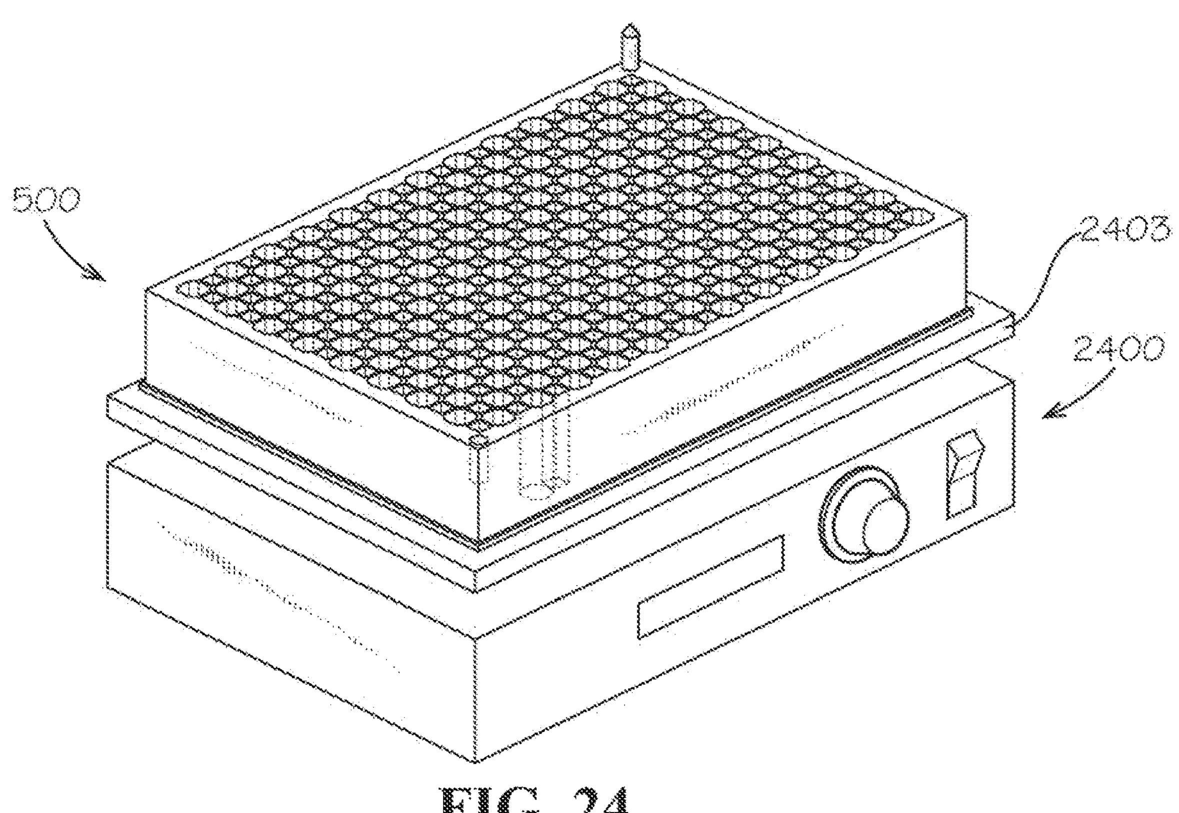
FIG. 24 illustrates an example of the assay microplate of FIG. 5 positioned on a tilting apparatus that causes the assay microplate to rotate about an axis to allow for the gravitational flow of liquid between the supply wells and the culture wells in accordance with various embodiments of the present disclosure.

FIG. 24 illustrates an example of the assay microplate 500 disposed on a tilting apparatus 2400 in accordance to various embodiments of the present disclosure. According to various examples, the assay microplate 500 may rest on a platform 2403 of otherwise flat surface of the tilting apparatus 2400. The tilting apparatus 2400 may be configured to rock or otherwise tilt the platform 2403 about an axis, thereby raising the height of one side of the assay microplate 500 relative to the opposing side of the assay microplate 500 and facilitating the flow of fluid from the supply well 512 of the perfusable unit 503 to the culture well 509, or vice versa. The tilting apparatus 2400 may comprise a conventional tilting system and may be manual or automated.

Turning now to FIG. 25 shown is an example of how the various microplates of the system of microplate may be mated to one another using automated systems, subsystems, or components in accordance to various examples of the present disclosure. In particular, FIG. 25 illustrates an example of the combination plate 300 being positioned over the assay microplate 500 via the use of a robotic apparatus 2500. The robotic apparatus 2500 may be configured to translate one or more microwell plates according to the present disclosure in physical space from one location to another. According to various examples, the robotic apparatus 2500 may manipulate or otherwise invert the transferring plate (e.g., combination microplate 300) over the receiving plate (e.g., assay microplate 500) and then mate the inverted transferring plate with the receiving plate in accordance to the embodiments of the present disclosure set forth above. Although FIG. 25 illustrates a combination plate 300 being mated to an assay microplate 500 using the robotic apparatus 2500, the starter microplate 100 may be mated to the combination microplate 300 using automated systems, subsystems, or components as can be appreciated. In other words, the robotic apparatus 2500 may be used to mate any of the respective microplates described above with respective other ones of the microplates as set forth herein.

In various examples, the robotic apparatus 2500 may include actuators or sonic transducers that are configured to apply ultrasonic or mechanical impulses to a transferring microplate that is positioned over a receiving microplate to cause the release of the surface tension in the wells of the transferring plate to allow the embryoid bodies to be transferred into the receiving plate, as can be appreciated. For example, once the robotic apparatus 2500 has achieved proper alignment and mating of the transferring plate to the receiving plate, the robotic apparatus 2500 may apply ultrasonic impulses to the transferring plate or to both mated plates to cause the transfer of cells, thereby minimizing the need for manual intervention and manipulation.

Cells

Cells according to the present disclosure may include stem cells (e.g., pluripotent stem cells), support cells, and/or the like.

Cells according to the present disclosure can be mammalian cells, in particular, human, rat, or mouse cells. Cells may include various immortalized cell lines or primary cell lines (e.g., HUVEC) that are typically used in research that are known to the skilled artisan. Cells according to the present disclosure can be pluripotent or multipotent stem cells (for example, without intending to be limiting, embryonic stem cells, induced pluripotent stem cells, or mesenchymal stem cells). In embodiments, stem cells according to the present disclosure can be mouse or human stem cells that are commercially available to the skilled artisan through outlets such as ATCC® or other commercial companies known in the art. Stem cells according to the present disclosure can also be human, mouse, or rat (or another organism) stem cells that were reprogrammed by the user from a source of primary cells utilizing any number of reprogramming methods and/or kits according to the art.

Support cells can be those support cells known to, for example, support stem cell culture. Without intending to be limiting, such cells can include mouse embryonic fibroblasts, induced pluripotent stem cell (iPSC) lines, embryonic stem cell lines (e.g., E5, E7, etc.), patient derived organoids (e.g., intestine, liver, Ipsc derived organoids, etc.), spheroids, embryoid bodies, tumoroids xenografts, various organisms (e.g., *drosophila*, zebrafish, etc.) or others known in the art.

The culture of various cells/cellular bodies at different stages of culture can be carried out using standard media and techniques as known in the art (for example, media including Dulbecco's modified eagle medium, stem cell media, mTeSR™, or variants thereof, fetal bovine serum, and leukemia inhibitory factor for mouse iPSCs). Differentiation of stem cells to primary cells of endodermal, ectodermal, and mesodermal lineage is also known and described in the art and can be employed according to methods of the present disclosure.

Hydrogels/Scaffolds

Hydrogels and/or scaffolds can be employed in microwell plates, systems, kits, and methods as described herein to facilitate the 3D culture, growth, and assay of cellular bodies as described herein.

In an embodiment, a hydrogel or scaffold as described herein can comprise Matrigel® (gelatinous protein mixture secreted by Engelbreth-Holm-Swarm mouse sarcoma cells; Corning® Life Sciences). In other aspects, hydrogels or scaffold as described herein can comprise one or more extracellular matrix components, for example a collagen or fibronectin, bioinks, gelatin, alginate, Biomimesys®, cellulose-based hydrogels, or other hydrogels or scaffolds as can be appreciated. In some examples, a scaffold-free solution may be used.

Methods

Figure 26:
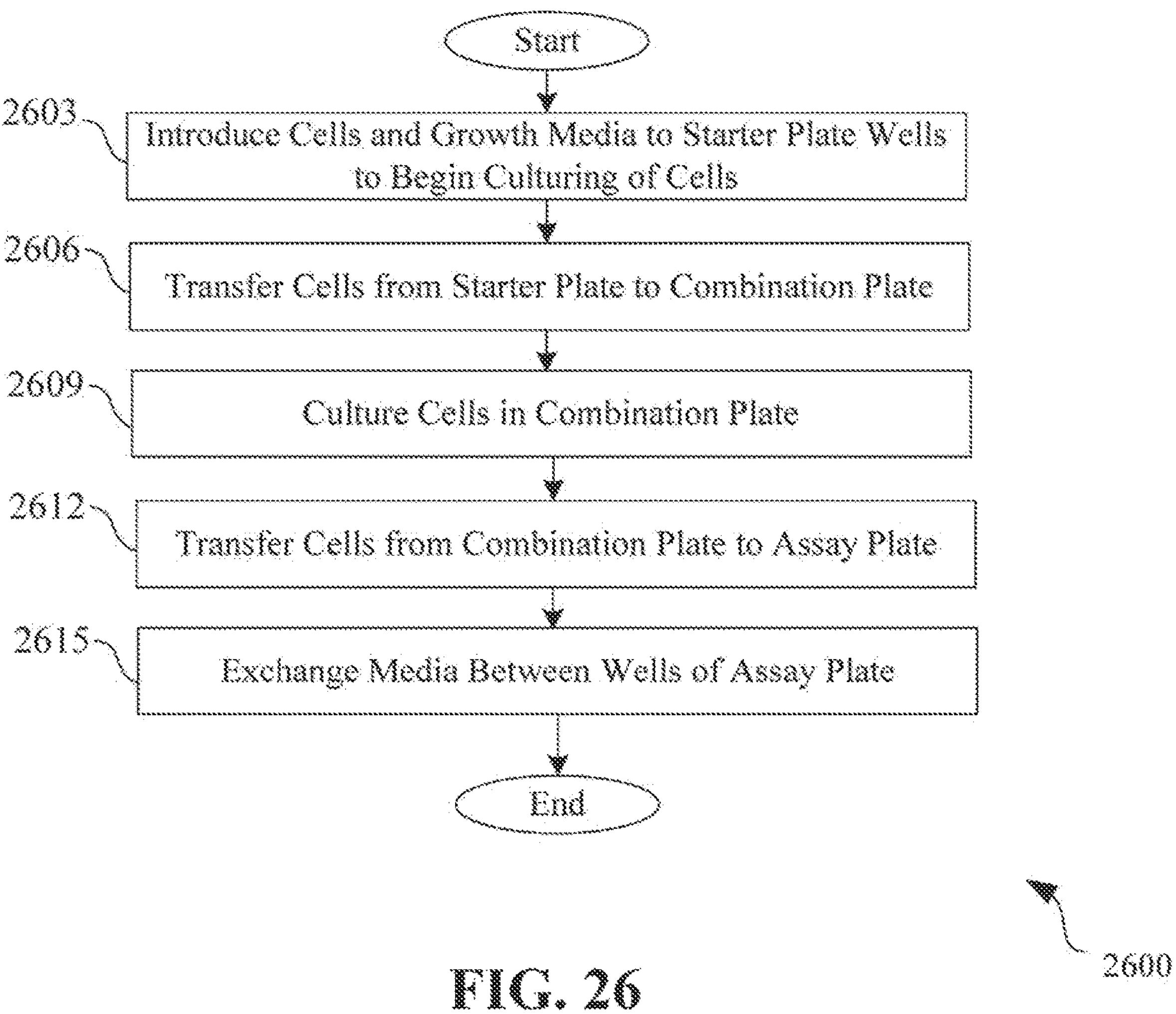
FIG. 26 illustrates a flowchart of an example method related to the use of the system of microplates during the various stages of growing and culturing of cells as described herein according to various embodiments of the present disclosure.

Described herein are methods of tissue culture, in particular methods of 3D tissue culture that employ microwell plates as described herein. FIG. 26 illustrates an example method related to the use of the microplate system of the present disclosure, in accordance to various embodiments.

At operation 2603, one or more cells can be cultured in one or more wells of a starter plate in the presence of cell growth media for a period of time in order to form one or more spheroids and/or embryoid bodies in the one or more wells of the starter plate.

At operation 2606, upon determining a desired stage of spheroid/embryoid body growth in the starter plate 100, the one or more spheroids and/or embryoid bodies can be transferred to a combination plate 300. The combination plate can comprise one or more spheroids and/or embryoid bodies in one more wells 303 corresponding to the one or more wells 303 in which cells are present in the starter plate 100. The transferring can be facilitated by mating the starter plate 100 and combination plate 300 together, and inverting the starter plate 100 in relationship to the combination plate 300 so that the cellular bodies in the one or more wells 303 of the starter plate 100 are transferred to the combination plate 300 by fluid flow driven by gravity. For example, the array of starter wells 106 of an inverted starter microplate 100 may be aligned with the array of combination wells 103 of a non-inverted combination microplate 300 and the mating collars 112, 312 may engage with one another to mate the plates to each other. In some embodiments, the transfer of cellular bodies from one plate to another can further be facilitated by agitating one or more of the mated plates. Such agitation could be manually (for example by the user shaking the mated plates from side to side), or could be done by the tilting or rocker apparatus 2400 and/or other device, for example an ultrasonic wave generator that applies ultrasonic energy to one or more of the mated plates.

At operation 2609, after transfer, culture in the combination plate 300 can commence so that the combined cellular bodies in the one or more wells can fuse together or the development of the combined cellular bodies progresses in some desired manner to a desired point.

At operation 2612, at a second desired stage of culture, the fused or otherwise developed cellular bodies can then be transferred from the one or more respective wells 303 of the combination plate 300 to the one or more respective wells 509, 512 of the assay plate 500. Such transfer can be facilitated by the mating the combination plate 300 and the assay plate 500 together, and inverting the combination plate 300 in relation to the assay plate 500 so that fluid flow is driven into the respective well[s] 509, 512 of the assay plate 500 by flow driven by gravity. In some embodiments, the transfer of cellular bodies from one plate to another can further be facilitated by agitating one or more of the mated plates. Such agitation could be accomplished manually (for example by the user shaking the mated plates from side to side), or could be done with a device, for example an ultrasonic wave generator that applies ultrasonic energy to one or more of the mated plates.

In embodiments, the cellular bodies can embed in a hydrogel disposed in the bottom of the wells of the assay plate 500 by passive means (such as falling as a result of gravity if the density of the cellular body allows for such) or active disposition, for example by embedding the cellular body into the hydrogel through pipetting (for example manual or robotic) or other suitable devices/methods that are known in the art. Without intending to be limiting, other suitable methods of depositing or otherwise embedding cellular bodies in the hydrogel/scaffold can further comprise bioink droplet printing, micro-contact printing, photolithography, dip pen nanolithography, and/or pipetting, among others.

At operation 2615, after embedding in the hydrogel in a growth well 509 of a perfusable unit of the assay plate 500, fresh media with fresh nutrients (glucose, amino acids, growth factors, hormones, and the like) can be delivered to the culture well 509 from the supply well 512 by fluid flow driven through a microchannel and/or gap of the perfusable unit 503 of the assay plate 500. Such fluid flow can further be facilitated by manually titling the plate at intervals desired by the user for periods of time desired by the user, or by other methods, such as by placement of the assay plate 500 on an automated tilting or rocker apparatus 2400 (which may or may not be present in a tissue culture incubator). Thereafter, the development or experimental process may proceed to completion.

In additional embodiments of methods as described herein, the transfer of cellular bodies from one plate to another (for example starter plate to combination plate, combination plate to assay plate, or starter plate to assay plate) can further be facilitated by agitating one or more of the mated plates. Such agitation could be manually (for example by the user shaking the mated plates from side to side), or could be done with a device, for example an ultrasonic wave generator that applies ultrasonic energy to one or more of the mated plates.

In embodiments, utilizing stem cells according to methods of the present disclosure, culture in the starter plate can involve typical culture protocols with typical reagents to maintain pluripotency or multipotency. Differentiation towards embryoid bodies, fused embryoid bodies, spheroids, organoids, and/or other multi-cellular bodies can be started in the starter plate and/or combination plate according to protocols known in the art with reagents known in the art. Such differentiation protocols and reagents are known in the art and omitted here as they would be ordinary knowledge to the skilled artisan.

According to embodiments of methods of the present disclosure, pluripotent or multipotent cells can be cultured in starter or combination plates according to protocols known in the art with reagents known in the art to form embryoid bodies. Following formation of embryoid bodies, the cellular bodies can be triggered to differentiate using extracellular cues towards organoids, or can be fused with other cellular bodies prior to differentiation. Such differentiation can take place in the starter plate, the combination plate, and/or the assay plate. In certain aspects, embryoid bodies can be embedded in the hydrogel/scaffold of the assay plate and then differentiated towards organoid into the assay plate, or the transition from embryoid body to organoid can take place in other plates, where only the final organoid is embedded in the hydrogel of the assay plate.

The developmental stages of stem cells, from stem cell culture and maintenance, to embryoid body formation, to differentiation to organoids can take place from starter plate to combination plate to assay plate, or other combinations/arrangements of steps/plates.

Systems

Also described herein are systems. Systems according to the present disclosure can comprise two or more types of microwell plates 100, 300, 500 as described herein. Systems according to the present disclosure can comprise three types of microwell plates 100, 300, 500 as described herein.

Systems as described herein can further comprise a rocking or tilting apparatus 2400. Such apparatus can have a flat surface configured to receive a microwell plate as described here that is operably connected to a motor that can "tilt" the microwell plate about an axis, thereby raising the height of one side relative to the opposing side and facilitating the flow of fluid from the supply well 512 of the perfusable unit 503 to the culture well 509, or vice versa.

Systems as described herein can further comprise a robotic apparatus 2500 that is configured to translate one or more microwell plates according to the present disclosure in physical space from one location to another. A robotic apparatus 2500 as described herein can further be configured to invert a microwell plate relative to a second microwell plate, and mate the two plates together.

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±20%, ±15%, ±10%, ±9%, ±8%, ±7%, ±6%, or ±5% A of the specified value, e.g., about 1" refers to the range of 0.8" to 1.2", 0.8" to 1.15", 0.9" to 1.1", 0.91" to 1.09", 0.92" to 1.08", 0.93" to 1.07", 0.94" to 1.06", or 0.95" to 1.05", unless otherwise indicated or inferred. It is understood that where "about," "approximate," or "at or about" is used before a quantitative value, the parameter also includes the specific quantitative value itself, unless specifically stated otherwise.

Any ratios, concentrations, amounts, and other numerical data can be expressed herein in a range format. Such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g., the phrase "x to y" includes the range from 'x' to Cy' as well as the range greater than 'x' and less than 'y'. The range can also be expressed as an upper limit, e.g., 'about x, y, z, or less' and should be interpreted to include the specific ranges of 'about x', 'about y', and 'about z' as well as the ranges of 'less than x', less than y', and 'less than z'. Likewise, the phrase 'x, y, z, or greater' should be interpreted to include the specific ranges of 'about x', 'about y', and 'about z' as well as the ranges of 'greater than x', greater than y', and 'greater than z'. In some aspects, the term "about" can include traditional rounding according to significant figures of the numerical value. In addition, the phrase "about 'x' to 'y'" includes "about 'x' to about "y."

The term "substantially" is meant to permit deviations from the descriptive term that do not negatively impact the intended purpose. All descriptive terms used herein are implicitly understood to be modified by the word "substantially," even if the descriptive term is not explicitly modified by the word "substantially."

Although any methods and materials similar or equivalent to those described herein can also be used in the practice or testing of the present disclosure, the various methods and materials suitable for use with the various disclosures disclosed herein are now described. Functions or constructions well-known in the art may not be described in detail for brevity and/or clarity.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A tissue culture kit for growing organoids, comprising:

a combination plate comprising an array of wells; and an assay plate comprising an array of perfusable units, a positioning of the array of perfusable units mirroring a positioning of the array of wells of the combination plate, thereby allowing each perfusable unit of the array of perfusable units to mate with a respective well of the array of wells of the combination plate, wherein each perfusable unit comprises a respective culture well and a respective supply well that are fluidly connected to one another and configured such that tilting the assay plate allows fluid exchange within the perfusable units without spilling fluid out of the respective culture well or respective supply well of each perfusable unit.

2. The tissue culture kit of claim 1, wherein the array of wells comprises a first array of wells, and further comprising:

a starter plate comprising a second array of wells, a positioning of the second array of wells of the starter plate mirroring a positioning of the first array of wells of the combination plate, thereby allowing respective wells of the first array of wells to mate with corresponding wells of the second array of wells.

3. The tissue culture kit of claim 2, wherein individual wells of the second array of wells of the starter plate comprise a respective starter plate mating collar being sized and shaped to create an interference fit with a respective combination plate mating collar of individual wells of the first array of wells.

4. The tissue culture kit of claim 3, wherein a size of the respective starter plate mating collar is smaller than a size of the respective combination plate mating collar.

5. The tissue culture kit of claim 2, wherein the starter plate mates with the combination plate to allow for a transfer of one or more cells from a respective well in the first array of wells to a respective corresponding well in the second array of wells.

6. The tissue culture kit of claim 1, wherein individual wells of the array of wells comprises a respective combination plate mating collar that is sized and shaped to create an interference fit with a respective opening of a respective well of a respective perfusable unit of the array of perfusable units.

7. The tissue culture kit of claim 1, wherein the combination plate mates with the assay plate to allow for a transfer of one or more cells from a respective corresponding well of the array of wells into a respective culture well of the assay plate.

8. The tissue culture kit of claim 1, wherein the combination plate and the assay plate each comprise a respective alignment pin and a respective alignment receiving aperture.

9. The tissue culture kit of claim 1, wherein the combination plate is inverted relative to the assay plate when interconnected with the assay plate.

10. The tissue culture kit of claim 1, wherein the assay plate further comprises an optically transparent viewing surface forming a bottom surface of the array of perfusable units.

11. The tissue culture kit of claim 10, wherein the optically transparent viewing surface is gas permeable.

* * * * *